United States Patent
Wunberg et al.

(10) Patent No.: US 7,709,491 B2
(45) Date of Patent: May 4, 2010

(54) SUBSTITUTED QUINAZOLINES AS ANTIVIRAL AGENTS, ESPECIALLY AGAINST CYTOMEGALOVIRUSES

(75) Inventors: Tobias Wunberg, Solingen (DE); Judith Baumeister, Wuppertal (DE); Mario Jeske, Solingen (DE); Susanne Nikolic, Monheim (DE); Frank Süßmeier, Wuppertal (DE); Holger Zimmermann, Wuppertal (DE); Rolf Grosser, Leverkusen (DE); Kerstin Henninger, Wuppertal (DE); Guy Hewlett, Wuppertal (DE); Jörg Keldenich, Wuppertal (DE); Dieter Lang, Velbert (DE); Tse-I Lin, Mechelen (BE)

(73) Assignee: Bayer Schering Pharma Aktiengesellschaft, Berlin (DE)

( * ) Notice: Subject to any disclaimer, the term of this patent is extended or adjusted under 35 U.S.C. 154(b) by 1032 days.

(21) Appl. No.: 10/534,138

(22) PCT Filed: Oct. 25, 2003

(86) PCT No.: PCT/EP03/11880

§ 371 (c)(1),
(2), (4) Date: May 5, 2006

(87) PCT Pub. No.: WO2004/041790

PCT Pub. Date: May 21, 2004

(65) Prior Publication Data

US 2006/0235032 A1    Oct. 19, 2006

(30) Foreign Application Priority Data

Nov. 8, 2002  (DE) ................................ 102 51 914

(51) Int. Cl.
A61K 31/517 (2006.01)
C07D 239/74 (2006.01)
C07D 405/10 (2006.01)

(52) U.S. Cl. ............... 514/266.1; 544/283; 514/266.3

(58) Field of Classification Search ............. 514/266.1, 514/266.3; 544/283
See application file for complete search history.

(56) References Cited

U.S. PATENT DOCUMENTS 7,271,260 B2 * 9/2007 Lee et al. .................... 544/119

FOREIGN PATENT DOCUMENTS

WO     9941253     8/1999

OTHER PUBLICATIONS

Vippagunta, S.R. et. al., "Crystalline solids", Advanced Drug Delivery Reviews, (2001), vol. 48, pp. 3-26.*
Wang, et al., Solid-Phase Synthesis of 3,4-Dihydroquinazoline, Tetra. Letts., vol. 38(50), 8651-8654 (1997).
Saito, et al., A Facile and Efficient Carbodiimide-Mediated Synthesis of Dihydroquinazolines via a Tandem Nucleophilic Addition-Intramolecular Hetero Conjugate Addition Annulation Strategy, Tetra. Letts., vol. 37(2), 209-212 (1996).

* cited by examiner

*Primary Examiner*—James O Wilson
*Assistant Examiner*—Tamthom N Truong
(74) *Attorney, Agent, or Firm*—Edwards Angell Palmer & Dodge LLP; Nicholas J. DiCeglie, Jr.; Barry Kramer

(57) ABSTRACT

The invention relates to substituted quinazolines and to methods for the production thereof, in addition to the use thereof in the production of medicaments for the treatment and/or prophylaxis of diseases, especially for use as antiviral agents, especially against cytomegaloviruses.

15 Claims, No Drawings

SUBSTITUTED QUINAZOLINES AS ANTIVIRAL AGENTS, ESPECIALLY AGAINST CYTOMEGALOVIRUSES

This application is the national stage of PCT/EP03/11880, filed Oct. 25, 2003, which claims priority from German patent application 10251914.5, filed Nov. 8, 2002.

The invention relates to substituted quinazolines and processes for their preparation, and to their use for producing medicaments for the treatment and/or prophylaxis of diseases, especially for use as antiviral agents, especially against cytomegaloviruses.

The synthesis of quinazolines is described in Saito T., et al. *Tetrahedron Lett.*, 1996, 37, 209-212.

Although structurally different agents with antiviral activity are available on the market, development of resistance is a regular possibility. Novel agents for better and effective therapy are therefore desirable.

One object of the present invention is therefore to provide novel compounds having the same or improved antiviral effect for the treatment of viral infectious diseases in humans and animals.

It has surprisingly been found that the substituted quinazolines described in the present invention have high antiviral activity.

The invention relates to compounds of the formula

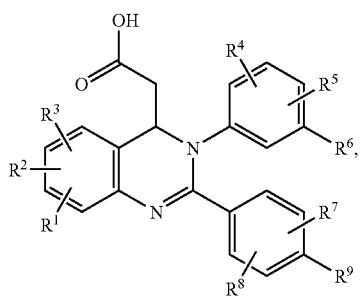

(I)

in which
R$^1$, R$^2$ and R$^3$ are independently of one another hydrogen, alkyl, alkoxy, carboxyl, alkylcarbonyl, alkoxycarbonyl, aminocarbonyl, trifluoromethyl, halogen, cyano, hydroxy or nitro,
R$^4$ and R$^5$ are independently of one another hydrogen, alkyl, alkoxy, cyano, halogen, nitro, trifluoromethyl or trifluoromethoxy,
R$^6$ is alkyl, cyano, halogen, nitro or trifluoromethyl,
R$^7$ and R$^8$ are independently of one another hydrogen, halogen, alkyl or alkoxy, and
R$^9$ is aryl or 1,3-benzodioxol-5-yl in which aryl and 1,3-benzodioxol-5-yl may be substituted by 1 to 3 substituents, where the substituents are selected independently of one another from the group consisting of alkoxy, alkylthio, carboxyl, alkylcarbonyl, alkoxycarbonyl, aminocarbonyl, trifluoromethyl, halogen, carbamoyl, cyano, hydroxy, amino, alkylamino, nitro and optionally hydroxy-substituted alkyl, and their salts, their solvates and the solvates of their salts.

Compounds of the invention are the compounds of the formula (I) and the salts, solvates and solvates of the salts thereof, and the compounds which are mentioned below as exemplary embodiment(s), and the salts, solvates and solvates of the salts thereof, where the compounds which are encompassed by formula (I) and are mentioned below are not already salts, solvates and solvates of the salts.

The compounds of the invention may, depending on their structure, exist in stereoisomeric forms (enantiomers, diastereomers). The invention therefore relates to the enantiomers or diastereomers and respective mixtures thereof. The stereoisomerically pure constituents can be isolated from such mixtures of enantiomers and/or diastereomers in a known manner.

Where the compounds of the invention can occur in tautomeric forms, the present invention encompasses all tautomeric forms.

Salts preferred for the purposes of the present invention are physiologically acceptable salts of the compounds of the invention. However, salts which are not themselves suitable for pharmaceutical applications but can be used for example to isolate or purify the compounds of the invention are also encompassed.

Physiologically acceptable salts of the compounds of the invention include acid addition salts of mineral acids, carboxylic acids and sulfonic acids, e.g. salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds of the invention also include salts of conventional bases such as, by way of example and preferably, alkali metal salts (e.g. sodium and potassium salts), alkaline earth metal salts (e.g. calcium and magnesium salts) and ammonium salts derived from ammonia or organic amines having 1 to 16 carbon atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates refer for the purposes of the invention to those forms of the compounds of the invention which form a complex in the solid or liquid state through coordination with solvent molecules. Hydrates are a special form of solvates in which coordination takes place with water.

Unless otherwise specified, for the purposes of the present invention the substituents have the following meaning:

Alkyl per se and "Alk" and "Alkyl" in alkoxy, alkylamino, alkylcarbonyl and alkoxycarbonyl are a linear or branched alkyl radical usually having 1 to 6 ("$C_1$-$C_6$-alkyl"), preferably 1 to 4, particularly preferably 1 to 3, carbon atoms, by way of example and preferably, methyl, ethyl, n-propyl, isopropyl, tert-butyl, n-pentyl and n-hexyl.

Alkoxy is, by way of example and preferably, methoxy, ethoxy, n-propoxy, isopropoxy, tert-butoxy, n-pentoxy and n-hexoxy.

Alkylcarbonyl is, by way of example and preferably, acetyl and propanoyl.

Alkylamino is an alkylamino radical having one or two (chosen independently of one another) alkyl substituents, by way of example and preferably, methylamino, ethylamino, n-propylamino, isopropylamino, tert-butylamino, n-pentylamino, n-hexylamino, N,N-dimethylamino, N,N-diethylamino, N-ethyl-N-methylamino, N-methyl-N-n-propylamino, N-isopropylamino-N-n-propylamino, N-t-butyl-N-methylamino, N-ethyl-N-n-pentylamino and N-n-hexyl-N-methylamino. $C_1$-$C_3$-Alkylamino is, for example, a monoalkylamino radical having 1 to 3 carbon atoms or a dialkylamino radical having in each case 1 to 3 carbon atoms per alkyl substituent.

Alkoxycarbonyl is, by way of example and preferably, methoxycarbonyl, ethoxycarbonyl, n-propoxycarbonyl, iso-propoxycarbonyl, tert-butoxycarbonyl, n-pentoxycarbonyl and n-hexoxycarbonyl.

Aryl is a mono- to tricyclic aromatic, carbocyclic radical ordinarily having 6 to 14 carbon atoms; by way of example and preferably phenyl, naphthyl and phenanthrenyl.

Halogen is fluorine, chlorine, bromine and iodine.

A * symbol on a carbon atom means that the compound is, in terms of the configuration at this carbon atom, in enantiopure form, by which is meant for the purposes of the present invention an enantiomeric excess of more than 90% (>90% ee).

Preference is given for the purposes of the present invention to compounds of the formula (I)

in which
$R^1$, $R^2$ and $R^3$ are independently of one another hydrogen, alkyl, alkoxy, carboxyl, alkylcarbonyl, alkoxycarbonyl, trifluoromethyl, halogen, cyano, hydroxy or nitro,
$R^4$ and $R^5$ are independently of one another hydrogen, alkyl, alkoxy, cyano, halogen, nitro or trifluoromethyl,
$R^6$ is alkyl, cyano, halogen, nitro or trifluoromethyl,
$R^7$ and $R^8$ are independently of one another hydrogen, halogen, alkyl or alkoxy and
$R^9$ is aryl in which aryl may be substituted by 1 to 3 substituents, where the substituents are selected independently of one another from the group consisting of alkyl, alkoxy, carboxyl, alkylcarbonyl, alkoxycarbonyl, trifluoromethyl, halogen, carbamoyl, cyano, hydroxy, amino, alkylamino and nitro, and their salts, their solvates and the solvates of their salts.

Preference is given for the purposes of the present invention to compounds of the formula (I)

in which
$R^1$, $R^2$ and $R^3$ are independently of one another hydrogen, fluorine, chlorine, cyano, hydroxy, aminocarbonyl or nitro,
$R^4$ and $R^5$ are independently of one another hydrogen, fluorine, alkyl or alkoxy,
$R^6$ is trifluoromethyl, isopropyl or tert-butyl,
$R^7$ and $R^8$ are independently of one another hydrogen, halogen, $C_1$-$C_3$-alkyl or $C_1$-$C_3$-alkoxy, and
$R^9$ is phenyl or 1,3-benzodioxol-5-yl in which phenyl may be substituted by 1 to 3 substituents, where the substituents are selected independently of one another from the group consisting of $C_1$-$C_6$-alkyl, $C_1$-$C_6$-alkoxy, carboxyl, $C_1$-$C_6$-alkylcarbonyl, $C_1$-$C_6$-alkoxycarbonyl, trifluoromethyl, fluorine, chlorine, bromine, cyano, hydroxy, amino, $C_1$-$C_6$-alkylamino and nitro, and their salts, their solvates and the solvates of their salts.

Preference is given for the purposes of the present invention to compounds of the formula (I)

in which
$R^1$, $R^2$ and $R^3$ are independently of one another hydrogen, fluorine, chlorine, cyano, hydroxy, aminocarbonyl or nitro,
$R^4$ and $R^5$ are independently of one another hydrogen, fluorine, alkyl or alkoxy,
$R^6$ is trifluoromethyl, isopropyl or tert-butyl,
$R^7$ and $R^8$ are independently of one another hydrogen, halogen, $C_1$-$C_3$-alkyl or $C_1$-$C_3$-alkoxy and
$R^9$ is phenyl, in which phenyl may be substituted by 1 to 3 substituents, where the substituents are selected independently of one another from the group consisting of $C_1$-$C_6$-alkyl, $C_1$-$C_6$-alkoxy, carboxyl, $C_1$-$C_6$-alkylcarbonyl, $C_1$-$C_6$-alkoxycarbonyl, trifluoromethyl, fluorine, chlorine, bromine, cyano, hydroxy, amino, $C_1$-$C_6$-alkylamino and nitro, and their salts, their solvates and the solvates of their salts.

Preference is given for the purposes of the present invention also to compounds of the formula (I)

in which
$R^1$ and $R^2$ are hydrogen,
$R^3$ is fluorine,
$R^4$ and $R^5$ are independently of one another hydrogen, fluorine or alkoxy,
$R^6$ is trifluoromethyl,
$R^7$ and $R^8$ are hydrogen and
$R^9$ is phenyl, in which phenyl may be substituted by 1 or 2 substituents, where the substituents are selected independently of one another from the group consisting of methyl, methoxy, fluorine and chlorine, and their salts, their solvates and the solvates of their salts.

Preference is given for the purposes of the present invention also to compounds of the formula (I) in which $R^1$ and $R^2$ are hydrogen.

Preference is given for the purposes of the present invention also to compounds of the formula (I) in which $R^3$ is bonded to the carbon atom in position 6 or in position 8 of the quinazoline structure.

Preference is given for the purposes of the present invention also to compounds of the formula (I) in which $R^3$ is bonded to the carbon atom in position 8 of the quinazoline structure.

Preference is given for the purposes of the present invention also to compounds of the formula (I) in which $R^3$ is fluorine, in particular is a fluorine bonded to the carbon atom in position 8 of the quinazoline structure.

Preference is given for the purposes of the present invention also to compounds of the formula (I) in which $R^4$ and $R^5$ are hydrogen.

Preference is given for the purposes of the present invention also to compounds of the formula (I) in which $R^4$ is hydrogen and $R^5$ is fluorine or alkoxy.

Preference is given for the purposes of the present invention also to compounds of the formula (I) in which $R^6$ is trifluoromethyl.

Preference is given for the purposes of the present invention also to compounds of the formula (I) in which $R^6$ is isopropyl or tert-butyl.

Preference is given for the purposes of the present invention also to compounds of the formula (I) in which $R^7$ and $R^8$ are hydrogen.

Preference is given for the purposes of the present invention also to compounds of the formula (I) in which $R^9$ is phenyl, in which phenyl may be substituted by 1 to 2 substituents, where the substituents are selected independently of one another from the group consisting of methyl, methoxy, fluorine and chlorine.

The invention further relates to a process for preparing the compounds of the formula (I), where compounds of the formula

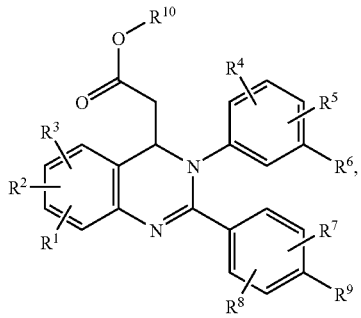

(II)

in which
R¹, R², R³, R⁴, R⁵, R⁶, R⁷, R⁸ and R⁹ have the meaning indicated above, and
R¹⁰ is alkyl, preferably methyl or ethyl, are reacted with bases.

The reaction generally takes place in inert solvents, preferably in a temperature range from room temperature to reflux of the solvents under atmospheric pressure.

Examples of bases are alkali metal hydroxides such as sodium, lithium or potassium hydroxide, or alkali metal carbonates such as cesium carbonate, sodium or potassium carbonate, where appropriate in aqueous solution, with preference for sodium hydroxide in water.

Examples of inert solvents are halohydrocarbons such as ethers such as 1,2-dimethoxyethane, dioxane, tetrahydrofuran, glycol dimethyl ether or diethylene glycol dimethyl ether, alcohols such as methanol, ethanol, n-propanol, isopropanol, n-butanol or tert-butanol, or mixtures of solvents, with preference for dioxane or tetrahydrofuran.

The compounds of the formula (II) are known or can be prepared by reacting compounds of the formula

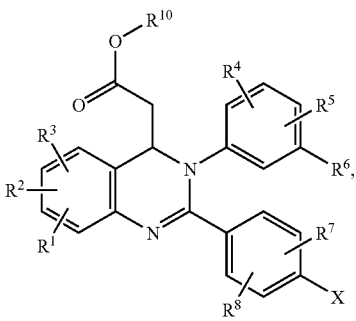

(III)

in which
R¹, R², R³, R⁴, R⁵, R⁶, R⁷, R⁸ and R¹⁰ have the meaning indicated above and
X is halogen, preferably bromine or chlorine, with compounds of the formula

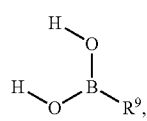

(IV)

in which
R⁹ has the meaning indicated above, under Suzuki coupling conditions.

The reaction generally takes place in inert solvents in the presence of a catalyst, where appropriate in the presence of an additional reagent, preferably in a temperature range from room temperature to 130° C. under atmospheric pressure.

Examples of catalysts are palladium catalysts usual for Suzuki reaction conditions, with preference for catalyst such as, for example, dichlorobis(triphenylphosphine)palladium, tetrakistriphenylphosphinepalladium(0), palladium(II)acetate, palladium(II) acetate/triscyclohexylphosphine or bis (diphenylphosphaneferrocenylpalladium(II) chloride.

Additional reagents are carried out for example potassium acetate, cesium carbonate, potassium carbonate or sodium carbonate, potassium tert-butoxide, cesium fluoride or potassium phosphate, with preference for additional reagents such as potassium acetate and/or aqueous sodium carbonate solution.

Examples of inert solvents are ethers such as dioxane, tetrahydrofuran or 1,2-dimethoxyethane, hydrocarbons such as benzene, xylene or toluene, or carboxamides such as dimethylformamide or dimethylacetamide, alkyl sulfoxides such as dimethyl sulfoxide, or N-methylpyrrolidone, with preference for dioxane.

The compounds of the formula (IV) are known or can be synthesized by known processes from the appropriate precursors.

The compounds of the formula (III) are known or can be prepared by reacting compounds of the formula

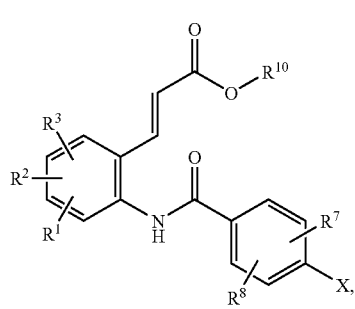

(V)

in which
R¹, R², R³, R⁷, R⁸, R¹⁰ and X have the meaning indicated above, with compounds of the formula

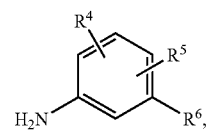

(VI)

in which
R⁴, R⁵ and R⁶ have the meaning indicated above, in the presence of phosphorus oxychloride.

The reaction generally takes place in inert solvents, preferably in a temperature range from 50° C. to reflux of the solvents under atmospheric pressure.

Examples of inert solvents are hydrocarbons such as benzene, xylene, toluene, hexane, cyclohexane or petroleum fractions, with preference for toluene.

Alternatively, the compounds of the formula (III) can be prepared in a two-stage synthetic process. In the first stage, the compounds of the formula (V) are heated with phosphorus oxychloride in an inert solvent, with preference for toluene, under reflux under atmospheric pressure. The solvent is removed. In the second stage, the compounds obtained in this way are reacted with compounds of the formula (VI) in an inert solvent, with preference for toluene, likewise under reflux under atmospheric pressure.

The compounds of the formula (VI) are known or can be synthesized by known processes from the appropriate precursors.

The compounds of the formula (V) are known or can be prepared by reacting compounds of the formula

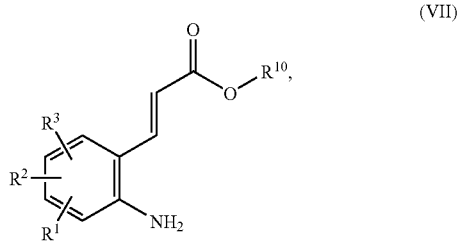

(VII)

in which
$R^1$, $R^2$, $R^3$ and $R^{10}$ have the meaning indicated above, with compounds of the formula

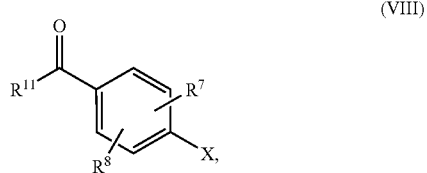

(VIII)

in which
$R^7$, $R^8$ and X have the meaning indicated above, and
$R^{11}$ is halogen, preferably chlorine, bromine or iodine, or hydroxy.

In the case where $R^{11}$ is hydroxy,
the reaction generally takes place in inert solvents in the presence of usual condensing agents, where appropriate in the presence of a base, preferably in a temperature range from room temperature to 50° C. under atmospheric pressure.

Examples of inert solvents are halohydrocarbons such as methylene chloride, trichloromethane, tetrachloromethane, trichloroethane, tetrachloroethane, 1,2-dichloroethane or trichloroethylene, ethers such as diethyl ether, methyl tert-butyl ether, dioxane, tetrahydrofuran, 1,2-dimethoxyethane, glycol dimethyl ether or diethylene glycol dimethyl ether, hydrocarbons such as benzene, xylene, toluene, hexane, cyclohexane or petroleum fractions, or carboxamides such as dimethylformamide or dimethylacetamide, alkyl nitriles such as acetonitrile, or heteroaromatic compounds such as pyridine, or ethyl acetate, with preference for tetrahydrofuran, 1,2-dichloroethane or methylene chloride.

Examples of usual condensing agents are carbodiimides such as, for example, N,N'-diethyl-, N,N'-dipropyl, N,N'-diisopropyl, N,N'-dicyclohexylcarbodiimide, N-(3-dimethylaminoisopropyl)-N'-ethylcarbodiimide hydrochloride (EDC), N-cyclohexylcarbodiimide-N'-propyloxymethyl-polystyrene (PS-carbodiimide) or carbonyl compounds such as carbonyldiimidazole, or 1,2-oxazolium compounds such as 2-ethyl-5-phenyl-1,2-oxazolium 3-sulfate or 2-tert-butyl-5-methylisoxazolium perchlorate, or acylamino compounds such as 2-ethoxy-1-ethoxycarbonyl-1,2-dihydroquinoline, or propanephosphonic anhydride, or isobutyl chloroformate, or bis(2-oxo-3-oxazolidinyl)phosphoryl chloride or benzotriazolyloxy-tri(dimethylamino)phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU), or 1-hydroxybenzotriazole (HOBt) or benzotriazol-1-yloxytris(dimethylamino)phosphonium hexafluorophosphate (BOP) or mixtures thereof.

Examples of bases are alkali metal carbonates such as, for example, sodium or potassium carbonate, or bicarbonate, or organic bases such as trialkylamines, for example triethylamine, N-methylmorpholine, N-methylpiperidine, 4-dimethylaminopyridine or diisopropylethylamine.

The combination of N-(3-dimethylaminoisopropyl)-N'-ethylcarbodiimide hydrochloride (EDC), 1-hydroxybenzotriazole (HOBt) and triethylamine in dimethylformamide or carbonyldiimidazole in 1,2-dichloroethane is particularly preferred.

In the case where $R^{11}$ is halogen,
the reaction generally takes place in inert solvents, where appropriate in the presence of a base, preferably in a temperature range from 0° C. to 50° C. under atmospheric pressure.

Examples of inert solvents are halohydrocarbons such as methylene chloride, trichloromethane, tetrachloromethane, trichloroethane, tetrachloroethane, 1,2-dichloroethane or trichloroethylene, ethers such as diethyl ether, methyl tert-butyl ether, dioxane, tetrahydrofuran, 1,2-dimethoxyethane, glycol dimethyl ether or diethylene glycol dimethyl ether, hydrocarbons such as benzene, xylene, toluene, hexane, cyclohexane or petroleum fractions, or carboxamides such as dimethylformamide or dimethylacetamide, alkyl nitriles such as acetonitrile, or heteroaromatic compounds such as pyridine, or ethyl acetate, with preference for tetrahydrofuran, dioxane or methylene chloride.

Examples of bases are alkali metal carbonates such as cesium carbonate, sodium or potassium carbonate, or other bases such as triethylamine or diisopropylethylamine, preferably diisopropylethylamine or triethylamine.

The compounds of the formula (VIII) are known or can be synthesized by known processes from the appropriate precursors.

The compounds of the formula (VII) are known or can be synthesized by known processes from the appropriate precursors, for example by a Heck reaction or a Wittig-Horner reaction as shown in the following synthesis schemes:

Heck Reaction:

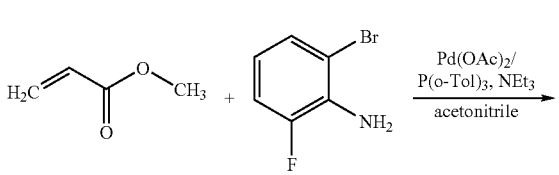

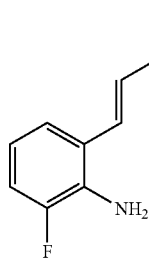

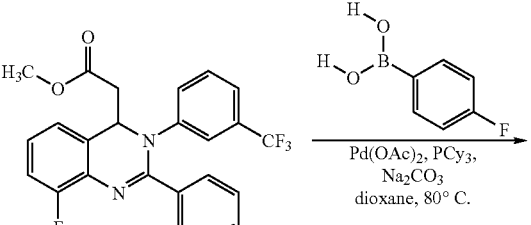

Wittig-Horner Reaction:

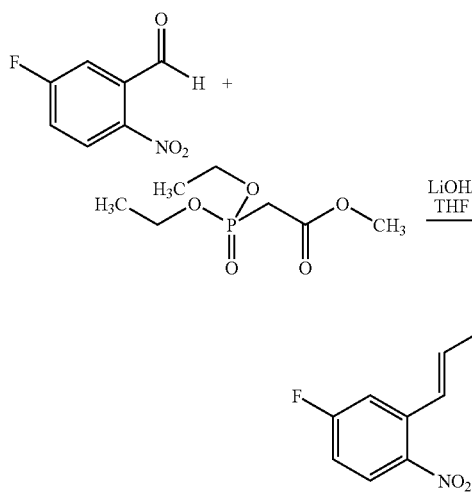

The precursors required therefor are known or can be synthesized by known processes from the appropriate precursors.

The preparation of the compounds of the invention can be illustrated by the following synthesis scheme.

Synthesis scheme

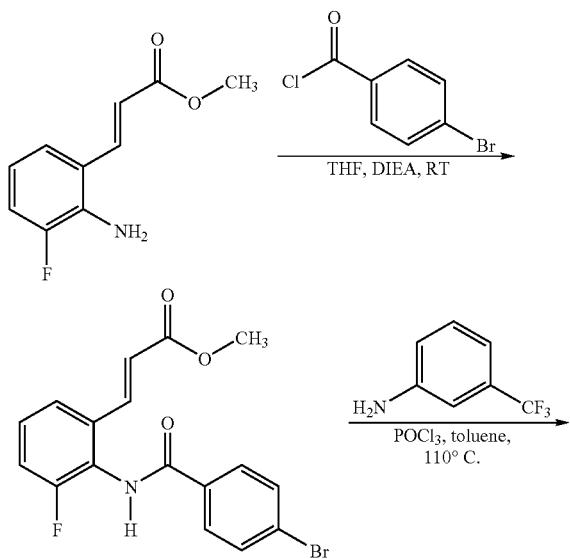

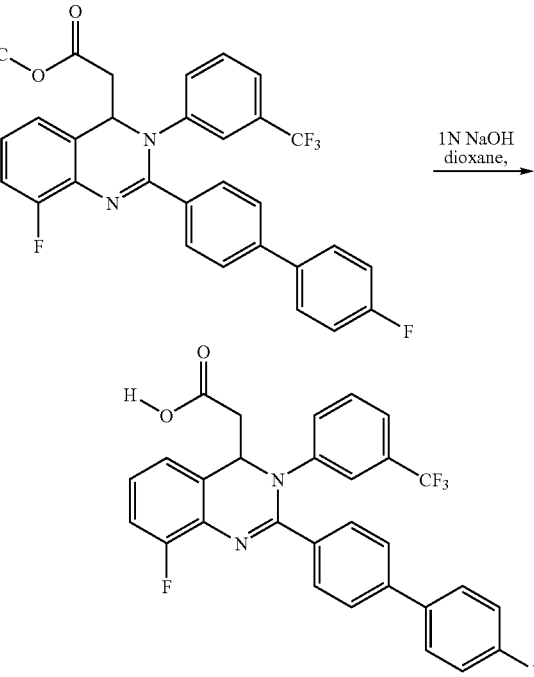

The compounds of the invention of the formula (I) show a surprising range of effects which could not have been predicted. They show an antiviral effect on representatives of the group of Herpes viridae (herpes viruses), in particular on cytomegaloviruses (CMV) especially on human cytomegalovirus (HCMV). They are therefore suitable for the treatment and/or prophylaxis of diseases, especially of infections with viruses, in particular the aforementioned viruses, and the infectious diseases caused thereby. A viral infection means hereinafter both an infection with a virus and a disease caused by infection with a virus.

The compounds of the formula (I) can, because of their particular properties, be used to produce medicaments which are suitable for the prophylaxis and/or treatment of diseases, especially viral infections.

Areas of indication which may be mentioned by way of example are:

1) Treatment and prophylaxis of HCMV infections in AIDS patients (retinitis, pneumonitis, gastrointestinal infections).
2) Treatment and prophylaxis of cytomegalovirus infections in bone-marrow and organ transplant patients who develop often life-threatening HCMV pneumonitis or encephalitis, and gastrointestinal and systemic HCMV infections.
3) Treatment and prophylaxis of HCMV infections in neonates and infants.
4) Treatment of an acute HCMV infection in pregnant women.

5) Treatment of HCMV infection in immunosuppressed patients associated with cancer and cancer therapy.

The compounds of the invention are preferably used to produce medicaments which are suitable for the prophylaxis and/or treatment of infections with a representative of the group of Herpes viridae, particularly a cytomegalovirus, in particular human cytomegalovirus.

The compounds of the invention can, because of their pharmacological properties, be employed alone and, if required, also in combination with other active ingredients, especially antiviral active ingredients such as, for example, gancyclovir or acyclovir for the treatment and/or prevention of viral infections, in particular of HCMV infections.

The present invention further relates to medicaments which comprise at least one compound of the invention, preferably together with one or more inert, non-toxic, pharmacologically acceptable excipients, and to the use thereof for the aforementioned purposes.

The compounds of the invention may have systemic and/or local effects. It can for this purpose be administered in a suitable way, such as, for example, by the oral, parenteral, pulmonary, nasal, sublingual, lingual, buccal, rectal, dermal, transdermal, conjunctival or otic route, or as implant or stent.

For these administration routes it is possible to administer the compounds of the invention in suitable administration forms.

Suitable for oral administration are administration forms which function according to the prior art and deliver the compounds of the invention rapidly and/or in modified fashion, and which contain the compounds of the invention in crystalline and/or amorphized and/or dissolved form, such as, for example, tablets (uncoated or coated tablets, for example having coatings which are resistant to gastric juice or are insoluble or dissolve with a delay and control the release of the compound of the invention), tablets which disintegrate rapidly in the mouth, or films/wafers, films/lyophylisates, capsules (for example hard or soft gelatin capsules), sugar-coated tablets, granules, pellets, powders, emulsions, suspensions, aerosols or solutions.

Parenteral administration can take place with avoidance of an absorption step (intravenous, intraarterial, intracardiac, intraspinal or intralumbar) or with inclusion of absorption (intramuscular, subcutaneous, intracutaneous, percutaneous, or intraperitoneal). Administration forms suitable for parenteral administration are, inter alia, preparations for injection and infusion in the form of solutions, suspensions, emulsions, lyophilizates and sterile powders.

Examples suitable for the other administration routes are pharmaceutical forms for inhalation (inter alia powder inhalers, nebulizers), nasal drops/solutions, sprays; tablets, films or capsules to be administered lingually, sublingually or buccally, suppositories, preparations for the eyes and ears, vaginal capsules, aqueous suspensions (lotions, shaking mixtures), lipophilic suspensions, ointments, creams, transdermal therapeutic systems, milk, pastes, foams, dusting powders, implants or stents.

The compounds of the invention can be converted into the stated administration forms. This can take place in a manner known per se by mixing with inert, nontoxic, pharmaceutically suitable excipients. These excipients include, inter alia, carriers (for example microcrystalline cellulose, lactose, mannitol), solvents (e.g. liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (e.g. antioxidants such as, for example, ascorbic acid), colours (e.g. inorganic pigments such as, for example, iron oxides) and masking tastes and/or odours.

It has generally proved advantageous to administer on intravenous administration amounts of about 0.001 to 10 mg/kg, preferably about 0.01 to 5 mg/kg, of body weight to achieve effective results, and the dosage on oral administration is about 0.01 to 25 mg/kg, preferably 0.1 to 10 mg/kg, of body weight.

It may nevertheless be necessary where appropriate to deviate from the amounts mentioned, specifically as a function of the body weight, administration route, individual response to the active ingredient, mode of preparation and time or interval over which administration takes place. Thus, it may be sufficient in some cases to make do with less than the aforementioned minimal amount, whereas in other cases the upper limit mentioned must be exceeded. It may in the event of administration of larger amounts be advisable to divide these into a plurality of individual doses over the day.

The percentage data in the following tests and examples are percentages by weight unless otherwise indicated; parts are parts by weight. Solvent ratios, dilution ratios and concentration data of liquid/liquid solutions are in each case based on volume.

A. EXAMPLES

Abbreviations Used:
$CD_3CN$ deuteroacetonitrile
conc. concentrated
DCI direct chemical ionization (in MS)
DCM dichloromethane
DIEA N,N-diisopropylethylamine (Hünig's base)
DMSO dimethyl sulfoxide
DMF N,N-dimethylformamide
EA ethyl acetate (acetic acid ethyl ester)
EI electron impact ionization (in MS)
ESI electrospray ionization (in MS)
h hour
HPLC high pressure, high performance liquid chromatography
LC-MS coupled liquid chromatography-mass spectroscopy
LDA lithium diisopropylamide
m.p. melting point
MS mass spectroscopy
NMR nuclear magnetic resonance spectroscopy
RP-HPLC reverse phase HPLC
RT room temperature
$R_t$ retention time (in HPLC)
sat. saturated
THF tetrahydrofuran
TLC thin layer chromatography General LC-MS and HPLC Methods:

Method 1 (HPLC): instrument: HP 1100 with DAD detection; column: Kromasil RP-18, 60 mm×2 mm, 3.5 µm; eluent A: 5 ml ($HClO_4$/l water, eluent B: acetonitrile; gradient: 0 min 2% B, 0.5 min 2% B 4.5 min 90% B, 6.5 min 90% B; flow rate: 0.75 ml/min; temp.: 30° C.; UV detection: 210 nm.

Method 2 (HPLC, enantiomer separation): chiral silica gel selector KBD 6136 (10 μm, 350×30 mm) based on the selector poly(N-methylacryloyl-L-leucine 1-menthylamide); temperature: 24° C.; flow rate 50 ml/min; UV detection: 254 nm; sample loaded in ethyl acetate; elution mixtures of isohexane (A)/ethyl acetate (B), e.g.: gradient:→0 min 40% B→9.0 min 40% B→9.01 min 100% B→12.0 min 100% B→-+12.01 min 40% B→15 min 40% B.

Method 3 (LCMS): instrument: Micromass Platform LCZ with HPLC Agilent series 1100; column: Grom-SIL120 ODS-4 HE, 50 mm×2.0 mm, 3 μm; eluent A: 1 l of water+1 ml of 50% formic acid, eluent B: 1 l of acetonitrile+1 ml of 50% formic acid; gradient: 0.0 min 100% A→0.2 min 100% A→2.9 min 30% A→3.1 min 10% A→4.5 min 10% A; oven: 55° C.; flow rate: 0.8 ml/min; UV detection: 208-400 nm.

Method 4 (HPLC, preparative separation): column: Crom-Sil C18, 250×30; flow rate: 50 ml/min; running time: 38 min; detection: 210 nm; eluent A=water, eluent B=acetonitrile; gradient: 10% B (3 min)→90% B (31 min)→90% B (34 min)→10% B (34.01 min).

Method 5 (HPLC): instrument: HP 1100 with DAD detection; column: Kromasil RP-18, 60 mm×2 mm, 1.0 μl; eluent A: 5 ml (HClO$_4$/l water, eluent B: acetonitrile; gradient: 0 min 2% B, 0.5 min 2% B 4.5 min 90% B, 9.0 min 90% B; flow rate: 0.75 ml/min; temp.: 30° C.; UV detection: 210 nm.

Method 6 (HPLC, enantiomer separation): chiral silica gel selector ZWE 840B (10 μm; column 250*20 mm) based on the selector poly(N-methacryloyl-L-leucine (+)-3-aminomethylpinanylamide); temperature: 24° C.; flow rate 25 min/min; UV detection: 280 nm; sample loaded in isohexane/ethyl acetate; elution mixture of isohexane/ethyl acetate 7:3 (vol/vol).

Method 7 (LCMS): MS instrument type: Micromass ZQ; HPLC instrument type: Waters Alliance 2790; column: Grom-Sil 120 ODS-4-HE 50 mm×2 mm, 3.0 μm; eluent B: acetonitrile+0.05% formic acid, eluent A: water+0.05% formic acid; gradient 0.0 min 5% B→2.0 min 40% B→4.5 min 90% B→5.5 min 90% B; oven: 45° C.; flow rate: 0.0 min 0.75 ml/min→4.5 min 0.75 ml/min→5.5 min 1.25 ml/min; UV detection: 210 nm.

Method 8: (LCMS): instrument: Micromass Quattro LCA, with HPLC Agilent series 1100; column: Grom-SIL120 ODA-4 HE, 50 mm×2.0 mm, 3 μm; eluent A: 1 l water+1 ml 50% formic acid, eluent B: 1 l acetonitrile+1 ml 50% formic acid; gradient: 0.0 min 100% A→0.2 min 100% A→2.9 min 30% A→3.1 min 10% A→4.5 min 10% A; oven: 55° C.; flow rate: 0.8 ml/min; UV detection: 208-400 nm.

Method 9 (HPLC, enantiomer separation): chiral silica gel selector KBD 8361 (10 μm; column 250*20 mm) based on the selector poly(N-methacryloyl-L-leucine 1-menthylamide); temperature: 24° C.; flow rate 25 ml/min; UV detection: 280 nm; sample loaded in isohexane/ethyl acetate; elution mixture of isohexane/ethyl acetate 1:1 (vol/vol).

Method 10 (HPLC, enantiomer separation): chiral silica gel selector KBD 6784 (10 μm; column 250*20 mm (based on the selector poly(N-methacryloyl-L-leucine 2,4-dimethylpentylamide); temperature: 24° C.; flow rate 20 m/min; UV detection: 270 nm; sample loaded in methyl tert-butyl ether; eluent: methyl tert-butyl ether.

Starting Compounds

General Method [A]: Synthesis of Substituted 2-Aminocinnamic Acid Derivatives by Heck Coupling from 2-Halo-Substituted Anilines 1.0 equivalent of an aryl halide with 1.6 of methyl acrylate, 2.0 equivalents of triethylamine, 0.03 equivalents of palladium(II) acetate and 0.03 equivalents of tri-o-tolylphosphine are introduced into acetonitrile (approx. 1M solution) in a one-neck flask. The mixture is stirred under reflux for 48 hours. After the reaction is complete (reaction checked by TLC), the solvent is removed. The residue is purified by chromatography on silica gel with cyclohexane/ethyl acetate=8:2 v/v.

Example 1A

Methyl(2E)-3-[2-amino-3-fluorophenyl)propenoate

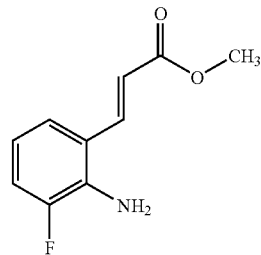

Starting from 42.00 g (221.04 mmol) 2-bromo-6-fluoroaniline, general method [A] results in 29.66 g (68% of theory) of product.

HPLC (method 1): $R_t$=4.14 min

MS (ESI-pos): m/z=196 (M+H)$^+$

Example 2A

Methyl(2E)-3-[2-amino-3-fluoro-5-methylphenyl]propenoate

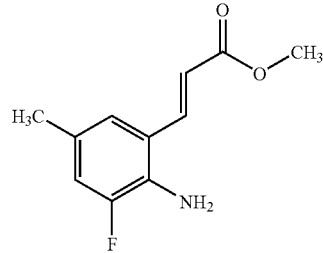

Starting from 1.9 g (9.31 mmol) of 2-bromo-4-methyl-6-fluoroaniline, general method [A] results in 502 mg (25% of theory) of product.

HPLC (method 1): $R_t$=4.31 min

MS (ESI-pos): m/z=210 (M+H)$^+$

General method [B]: Acylation of the 2-Aminocinnamic Esters with Benzoyl Chlorides 25.6 mmol of the 2-aminocinnamic ester and 25.6 mmol of Hünig's base are introduced into 200 ml of THF, the acid chloride is added at room temperature, and the mixture is stirred for 16 h. The solvent is then removed in vacuo, and the residue is taken up in dichloromethane. A precipitate is formed thereby and is stirred with dichloromethane and filtered off with suction. The crystals are then suspended in water, stirred, filtered off with suction and dried in vacuo.

Example 3A

Methyl(2E)-3-{2-[(4-bromobenzoyl)amino]-3-fluorophenyl}-2-propenoate

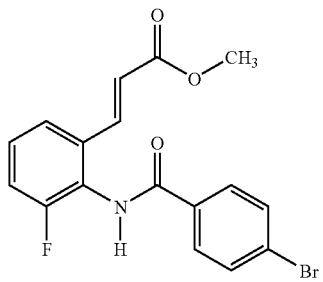

Starting from 5.0 g (25.6 mmol) of aminocinnamic ester from Example 1A, general method [B] results in 7.77 g (79% of theory) of product.

HPLC (method 1): $R_t$=4.48 min

Example 4A

Methyl(2E)-3-{2-[(4-bromo-2-fluorobenzoyl)amino]-3-fluorophenyl}-2-propenoate

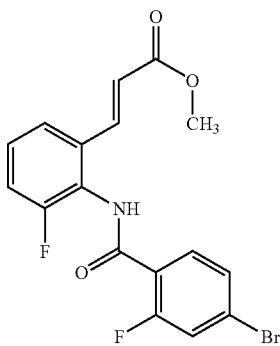

Starting from 162 mg (0.83 mmol) of aminocinnamic ester from Example 1A, general method [B] results in 148 mg (45% of theory) of product.

HPLC (method 1): $R_t$=4.64 min

Example 5A

Methyl(2E)-3-{2-[(4-bromobenzoyl)amino]-3-fluoro-5-methylphenyl}-2-propenoate

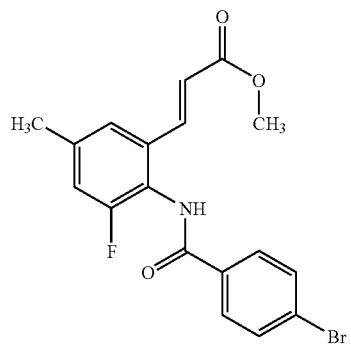

Starting from 536 mg (2.56 mmol) of aminocinnamic ester from Example 2A, general method [B] results in 700 mg (62% of theory) of product.

HPLC (method 1): $R_t$=4.70 min

MS (DCI): m/z=409 (M+NH$_4$)$^+$

General method [C]: Cyclization of the 2-Aminoacylcinnamic Esters with Anilines

Variant 1:

79.3 mmol of the 2-aminoacylcinnamic ester and 475.9 mmol of the aniline and 238.0 mmol of phosphorus oxychloride are introduced into 300 ml of toluene at room temperature. The suspension is heated (bath temperature 120-125° C.) with vigorous stirring under reflux for 24-72 h. Conversion is followed by thin-layer chromatogram or HPLC, with new quantities of aniline and phosphorus oxychloride being added every 24 h. The solvent is then removed in vacuo, and the residue is taken up in dichloromethane. The product is purified by chromatography on silica gel with cyclohexane/ethyl acetate mixtures. If the product crystallizes on the silica gel during the purification, it is isolated with pure methanol where appropriate after washing the silica gel with pure ethyl acetate.

Variant 2:

As alternative to variant 1, firstly the 2-aminoacylcinnamic ester is reacted with phosphorus oxychloride in toluene under reflux for 24 h, the mixture is concentrated, then the aniline is added, and the reaction mixture is again heated under reflux in toluene for 24 h. Working up takes place as described for variant 1.

Variant 3:

As alternative to variants 1 and 2, 1 equivalent of 2-acylaminocinnamic ester from Example 3A are suspended in toluene, and 10 equivalents of phosphoryl chloride are added. Stirring under reflux overnight is followed by evaporation to dryness and taking up the residue in toluene. 3 equivalents of aniline are then added to the boiling mixture, which is again stirred under reflux overnight. Removal of the solvent by distillation is followed by dissolving in dichloromethane and washing with 1N hydrochloric acid and sodium bicarbonate solution. The target compound is obtained after drying and purification by chromatography.

Example 6A

Methyl{2-[(4-bromophenyl)-8-fluoro-3-[3-(trifluoromethyl)phenyl]-3,4-dihydro-4-quinazolinyl}acetate

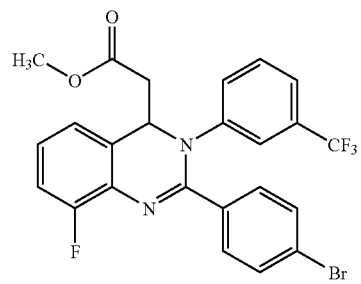

Starting from 30.0 g (79.3 mmol) of 2-acylaminocinnamic ester from Example 3A, general method [C-variant 1] and elution of the product from the silica gel column with cyclohexane, cyclohexane/ethyl acetate 20:1, cyclohexane/ethyl acetate 20:1.5, cyclohexane/ethyl acetate 2:1, cyclohexane/ethyl acetate 1:1, ethyl acetate, and methanol result in 39.3 g of contaminated product. The purification is therefore repeated by chromatography on silica gel, resulting in 11.5 g (55% of theory) of product.

HPLC (method 1): $R_t$=4.66 min

Example 7A

Methyl{2-(4-bromo-2-fluorophenyl)-8-fluoro-3-[3-trifluoromethyl)phenyl]-3,4-dihydro-4-quinazolinyl}acetate

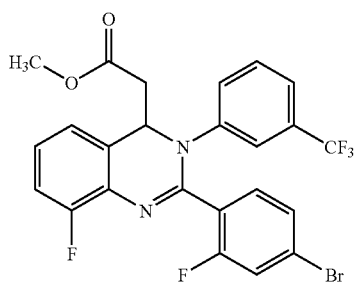

Starting from 90 mg (0.23 mmol) of 2-acylaminocinnamic ester from Example 4A, general method [C-variant 1] results in 35 mg (29% of theory) of product.

HPLC (method 1): $R_t$=4.66 min

Example 8A

Methyl{2-(4-bromophenyl)-8-fluoro-3-[2-fluoro-5-(trifluoromethyl)phenyl]-3,4-dihydro-4-quinazolinyl}acetate

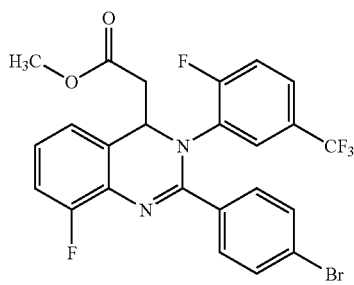

Starting from 1.0 g (2.64 mmol) of 2-acylaminocinnamic ester from Example 3A, general method [C-variant 1] results in 394 g (28% of theory) of product.

HPLC (method 1): $R_t$=4.71 min

MS (ESI-pos): m/z=539 (M+H)$^+$

Example 9A

Methyl{2-(4-bromophenyl)-8-fluoro-3-[4-fluoro-3-(trifluoromethyl)phenyl]-3,4-dihydro-4-quinazolinyl}acetate

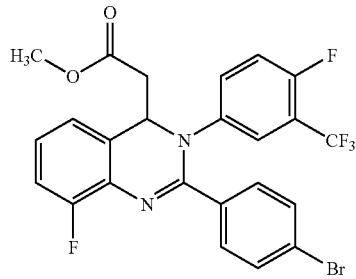

Starting from 500 g (1.32 mmol) of 2-acylaminocinnamic ester from Example 3A, general method [C-variant 1] results in 610 mg (68% of theory) of product.

HPLC (method 1): $R_t$=4.70 min
MS (ESI-pos): m/z=541 (M+H)$^+$

Example 10A

Methyl{2-(4-bromophenyl)-8-fluoro-6-methyl-3-[3-trifluoromethyl)phenyl]-3,4-dihydro-4-quinazolinyl}acetate

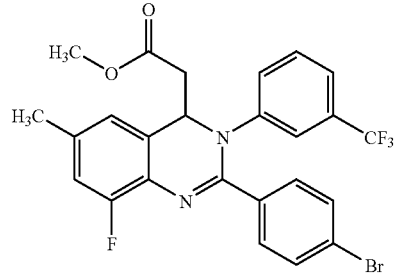

Starting from 700 mg (1.79 mmol) of 2-acylaminocinnamic ester from Example 5A, general method [C-variant 1] results in 1.23 g (quantitative) of product.

HPLC (method 1): $R_t$=4.70 min
MS (ESI-pos): m/z=535 (M+H)$^+$

Example 11A

Methyl{2-(4-bromophenyl)-8-fluoro-3-[2-methoxy-5-(trifluoromethyl)phenyl]-3,4-dihydroquinazolin-4-yl}acetate

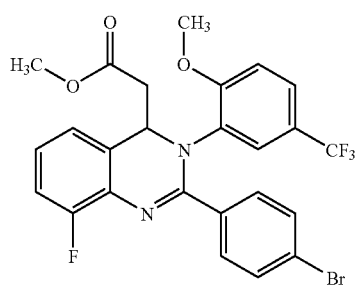

Starting from 260 mg (0.47 mmol) of 2-acylaminocinnamic ester from Example 3A, general method [C-variant 3] results in 64 mg (23% of theory) of product.

HPLC (method 7): $R_t$=2.97 min

Example 12A

Methyl{2-(4-bromophenyl)-8-fluoro-3-(5-tert-butyl-2-methoxyphenyl)-3,4-dihydroquinazolin-4-yl}acetate

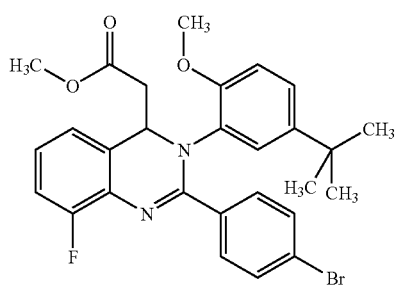

Starting from 2500 mg (6.61 mmol) of 2-acylaminocinnamic ester from Example 5A, general method [C-variant 2) results in 417 mg (12% of theory) of product.

HPLC (method 5): $R_t$=4.84 min
MS (ESI-pos): m/z=539 (M+H)$^+$

Example 13A

Methyl{3-(4-bromophenyl)-8-fluoro-3-[2-trifluoromethoxy)-5-(trifluoromethyl)phenyl]-3,4-dihydroquinazolin-4-yl}acetate

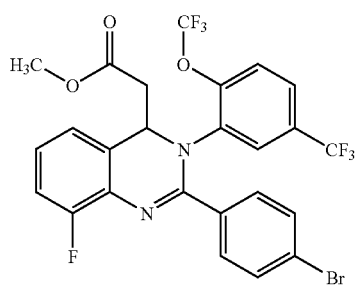

Starting from 181 mg (0.46 mmol) of 2-acylaminocinnamic ester from Example 5A, general method [C-variant 2] results in 150 mg (53% of theory) of product.

HPLC (method 5): $R_t$=5.02 min
MS (ESI-pos): m/z=621 (M+H)$^+$

General method [D]: Synthesis of Biphenyls by Suzuki Coupling 1.25 mmol of bromide, 1.50 mmol of boronic acid, 0.09 mmol of palladium(II) acetate, 0.15 mmol of triscyclohexylphosphine and 1.5 mol of sodium carbonate are introduced into 18 ml of a dioxane/water mixture (5:1 v/v), and the mixture is heated at 80° C. while stirring vigorously for 16 h.

The mixture is then filtered through a filter plate, the mother liquor is concentrated in vacuo, and the product is purified by preparative HPLC (method 4) or by chromatography on silica gel with cyclohexane/ethyl acetate mixtures.

Example 14A

Methyl{8-fluoro-2-(4'-fluoro-1,1'-biphenyl-4-yl)-3-[3-trifluoromethyl)phenyl-3,4-dihydro-4-quinazolinyl}acetate

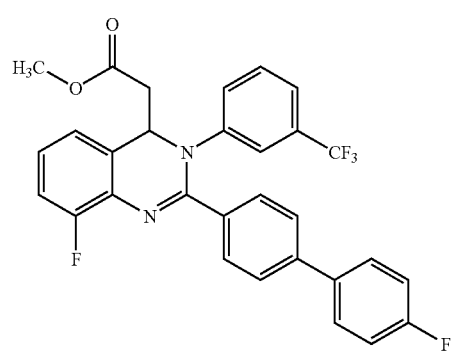

Starting from 650 mg (1.25 mmol) of the bromide from Example 6A, general method [D] and purification by preparative HPLC (method 4) result in 480 mg (72% of theory) of product.

HPLC (method 1): $R_t$=4.87 min

Example 15A

Methyl{8-fluoro-2-(3'-methyl-1,1'-biphenyl-4-yl)-3-[3-trifluoromethyl)phenyl]-3,4-dihydro-4-quinazolinyl}acetate

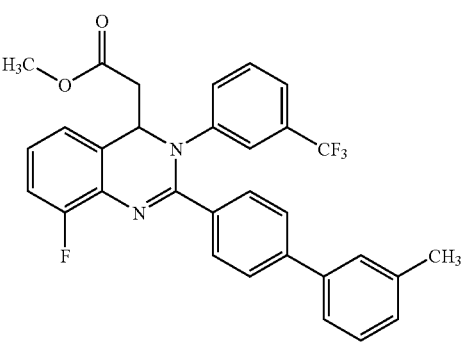

Starting from 5.0 g (9.59 mmol) of the bromide from Example 6A, general method [D] and chromatography on silica gel with cyclohexane/ethyl acetate 9:1 (v/v) and cyclohexane/ethyl acetate 8:1 (v/v) result in 1.89 g (37% of theory) of product.

HPLC (method 1): $R_t$=4.87 min

Example 16A

Methyl{8-fluoro-2-(4'-fluoro-3'-methyl-1,1'-biphenyl-4-yl)-3-[3-trifluoromethyl)phenyl]-3,4-dihydro-4-quinazolinyl}acetate

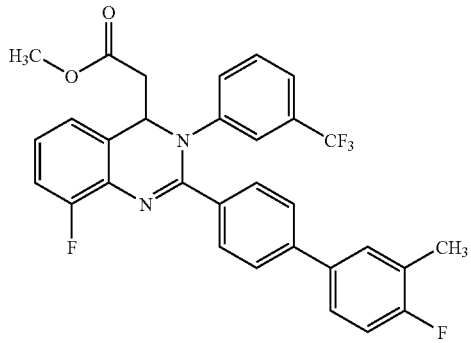

Starting from 150 mg (0.29 mmol) of the bromide from Example 6A, general method [D] and purification by preparative HPLC (method 4) result in 101 mg (64% of theory) of product.

HPLC (method 1): $R_t$=4.94 min

Example 17A

Methyl{8-fluoro-2-(3'-fluoro-1,1'-biphenyl)-3-[3-trifluoromethyl)phenyl]-3,4-dihydro-4-quinazolinyl}acetate

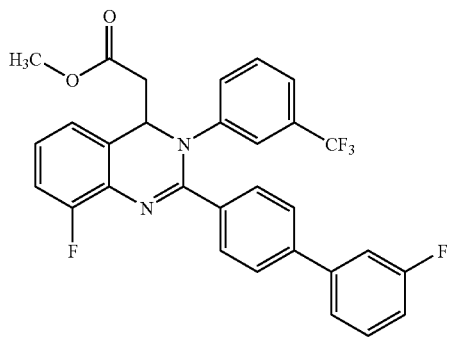

Starting from 150 mg (1.25 mmol) of the bromide from Example 6A, general method [D] and purification by preparative HPLC (method 4) result in 118 mg (76% of theory) of product.

Example 18A

Methyl{2-(3,4'-difluoro-1,1'-biphenyl-4-yl)-8-fluoro-3-[3-(trifluoromethyl)phenyl]-3,4-dihydro-4-quinazolinyl)acetate

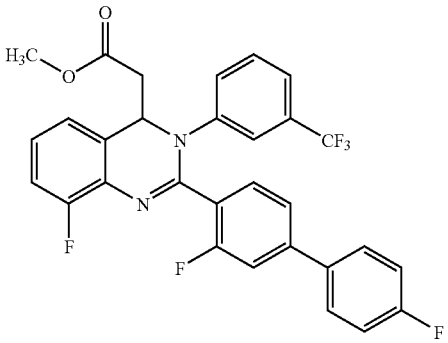

Starting from 30 mg (0.06 mmol) of the bromide from Example 7A, general method [D] and purification by preparative HPLC (method 4) result in 17 mg (55% of theory) of product.

HPLC (method 1): $R_t$=4.83 min

Example 19A

Methyl{2-[4-(1,3-benzodioxol-5-yl)phenyl]-8-fluoro-3-[2-methoxy-5-(trifluoromethyl)phenyl]-3,4-dihydro-4-quinazolinyl}acetate

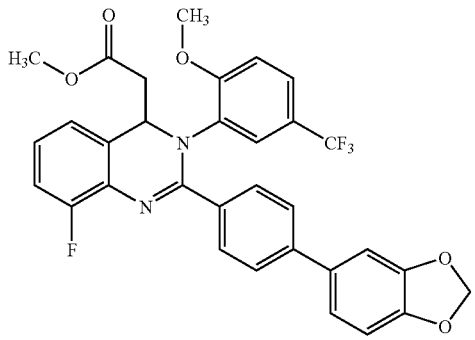

Starting from 56 mg (0.09 mmol) of the bromide from Example 11A, general method [D] and purification by preparative HPLC (method 4) result in 52 mg (92% of theory) of product.

HPLC (method 7): $R_t$=2.70 min

Example 20A

Methyl{2-[4-(4-fluorophenyl)phenyl]-8-fluoro-3-[2-methoxy-5-(trifluoromethyl)phenyl]-3,4-dihydro-4-quinazolinyl}acetate

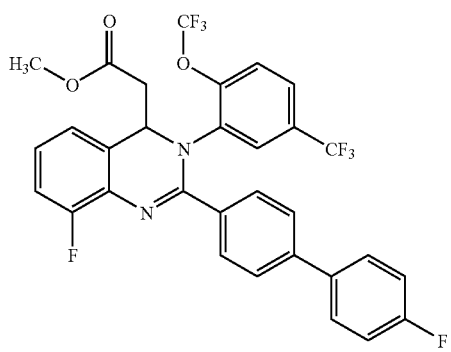

Starting from 500 mg (0.91 mmol) of the bromide from Example 11A, reaction in analogy to general method [D] with 152.27 mg (1.09 mmol) of 4-fluorophenylboronic acid, 31.83 mg (0.05 mmol) of bis(triphenylphosphine)palladium(II) chloride and 115.34 mg (1.09 mmol) of sodium carbonate in 10 ml of 1,2-dimethoxyethane and 0.5 ml of water results in 370.7 mg (72% of theory) of the target compound.

HPLC (method 1): $R_t$=4.8 min
MS (ESI-pos): m/z=567 (M+H)$^+$

Example 21A

Methyl{2-[4-(3-methylphenyl)phenyl]-8-fluoro-3-[2-methoxy-5-(trifluoromethyl)phenyl]-3,4-dihydro-4-quinazolinyl}acetate

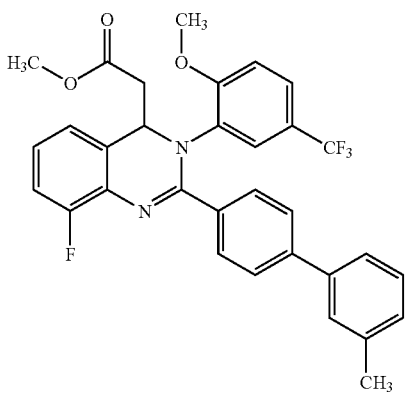

Starting from 1.00 g (1.81 mmol) of the bromide from Example 1A, reaction in analogy to general method [D] with 0.30 g (2.18 mmol) of 3-methylphenylboronic acid, 0.06 g (0.09 mmol) of bis(triphenylphosphine)palladium(II) chloride and 0.23 g (2.18 mmol) of sodium carbonate in 20 ml of 1,2-dimethoxyethane and 1 ml of water results in 450.5 mg (44% of theory) of the target compound.

HPLC (method 1): $R_t$=4.9 min
MS (ESI-pos): m/z=563 (M+H)$^+$

Example 22A

Methyl{2-[4-(3-methoxyphenyl)phenyl]-8-fluoro-3-[2-methoxy-5-(trifluoromethyl)phenyl]-3,4-dihydro-4-quinazolinyl}acetate

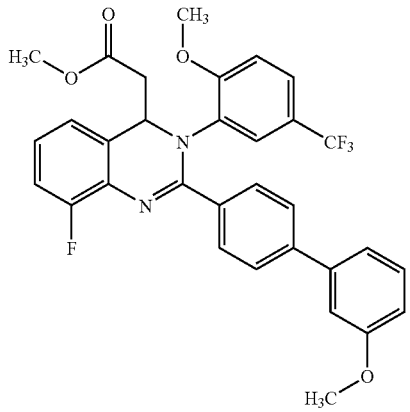

Starting from 1.00 g (1.81 mmol) of the bromide from Example 11A, reaction by general method [D] with 0.33 g (2.18 mmol) of 3-methoxyphenylboronic acid, 0.06 g (0.09 mmol) of bis(triphenylphosphine)palladium(II) chloride and 0.23 g (2.18 mmol) of sodium carbonate in 20 ml of 1,2-dimethoxyethane and 1 ml of water results in 466 mg (44% of theory) of the target compound.

HPLC (method 1): $R_t$=4.7 min
MS (ESI-pos): m/z=579 (M+H)$^+$

Example 23A

Methyl{2-[4-(3-fluorophenyl)phenyl]-8-fluoro-3-[2-methoxy-5-(trifluoromethyl)phenyl]-3,4-dihydro-4-quinazolinyl}acetate

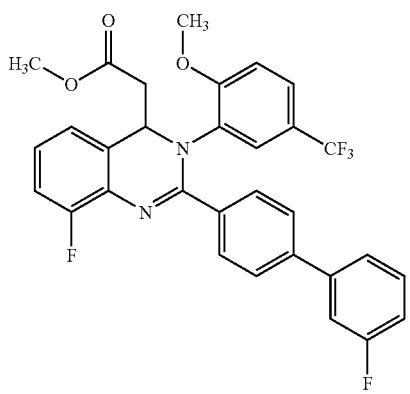

Starting from 100 mg (0.18 mmol) of the bromide from Example 11A, reaction by general method [D] with 30.5 mg (0.22 mmol) of 3-fluorophenylboronic acid, 6.37 mg (0.01 mmol) of bis(triphenylphosphine)palladium(II) chloride and 23.07 mg (0.22 mmol) of sodium carbonate in 10 ml of 1,2-dimethoxyethane and 0.1 ml of water results in 22.6 mg (22% of theory) of the target compound.

HPLC (method 5): $R_t$=4.9 min
MS (ESI-pos): m/z=567 (M+H)$^+$

Examples 24A to 44A in table 1 are prepared in analogy to general method [D].

TABLE 1

| Example | Structure | Molecular weight | HPLC R$_t$ [min] | HPLC/LCMS-method | m/z (M + H)$^+$ |
|---|---|---|---|---|---|
| 24A | 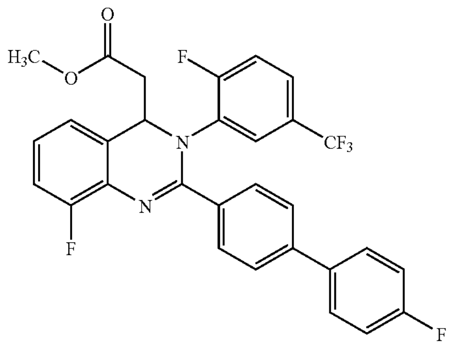 | 554.5 | 4.81 | 1 | 555 |
| 25A | 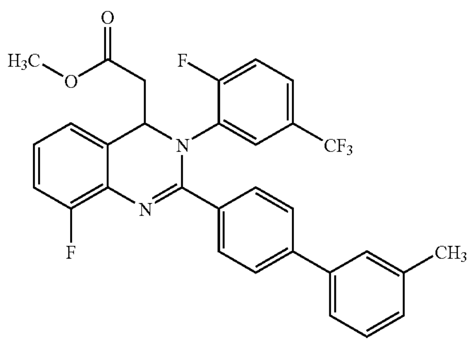 | 550.5 | 4.92 | 1 | 551 |
| 26A | 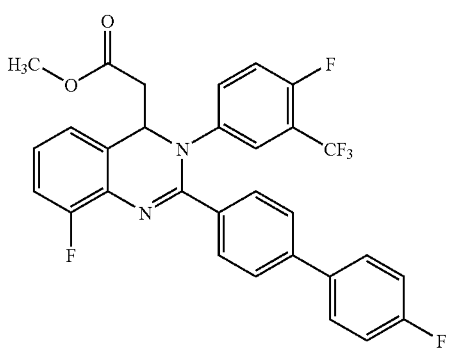 | 554.5 | 4.30 | 3 | 555 |
| 27A | 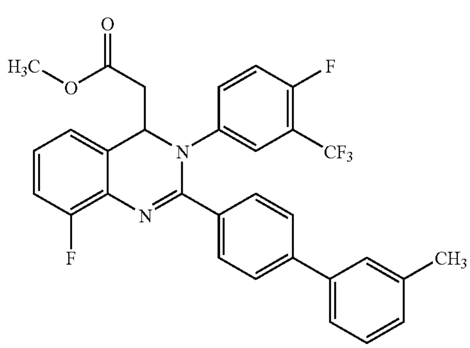 | 550.5 | 5.00 | 1 | 551 |

TABLE 1-continued
| Example | Structure | Molecular weight | HPLC R$_t$ [min] | HPLC/LCMS-method | m/z (M + H)$^+$ |
|---|---|---|---|---|---|
| 28A | 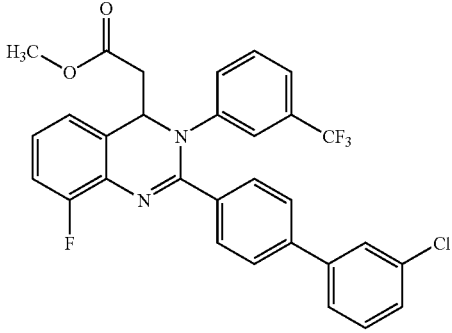 | 552.9 | 4.90 | 1 | 553 |
| 29A | 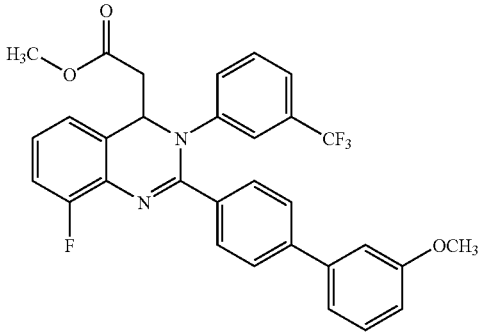 | 548.5 | 4.75 | 1 | 549 |
| 30A | 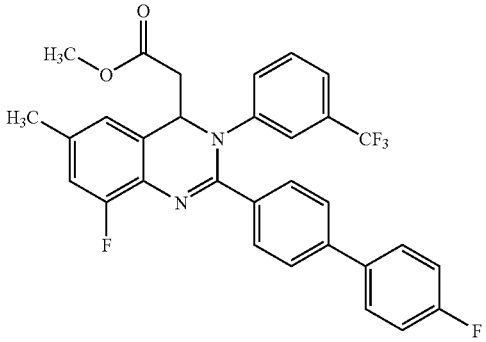 | 550.5 | 4.91 | 1 | 551 |
| 31A | 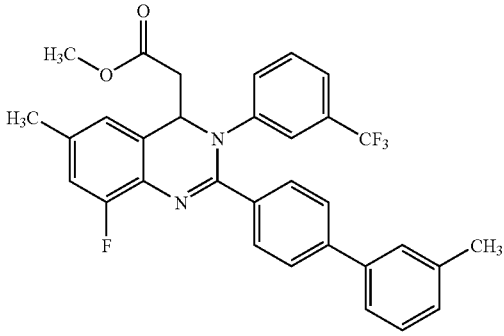 | 546.5 | 5.03 | 1 | 547 |

TABLE 1-continued

| Example | Structure | Molecular weight | HPLC R$_t$ [min] | HPLC/LCMS-method | m/z (M + H)$^+$ |
|---------|-----------|------------------|------------------|------------------|-----------------|
| 32A | 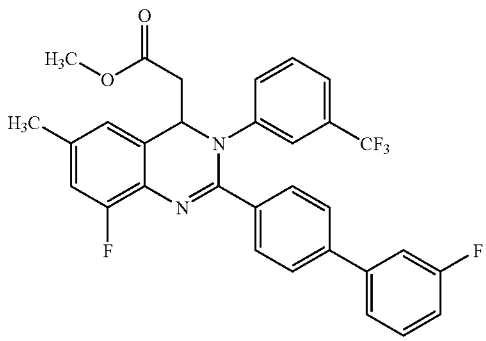 | 550.5 | 4.91 | 1 | 550 |
| 33A | 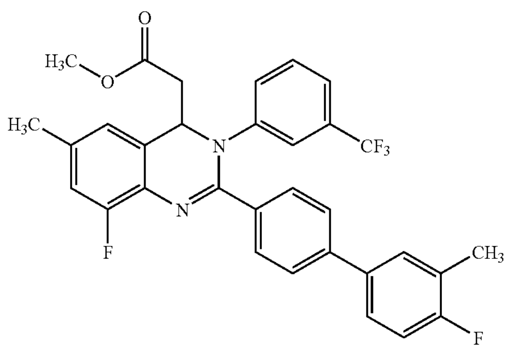 | 564.5 | 5.04 | 1 | 565 |
| 34A | 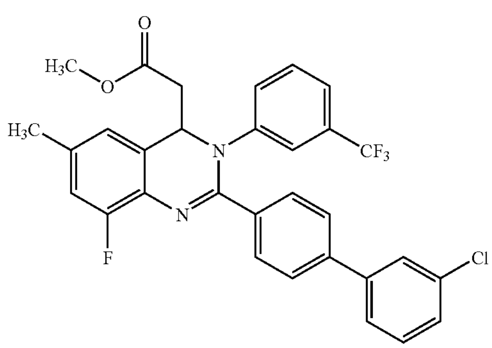 | 567 | 5.11 | 1 | 567 |
| 35A | 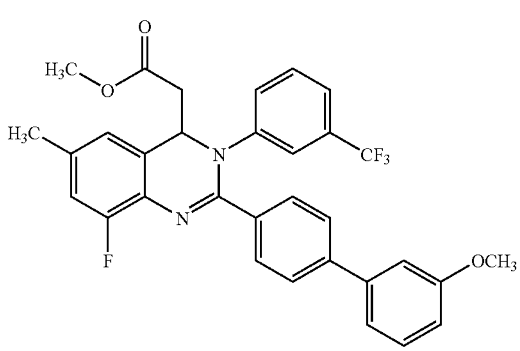 | 562.5 | 4.89 | 1 | 563 |

TABLE 1-continued

| Example | Structure | Molecular weight | HPLC R$_t$ [min] | HPLC/LCMS-method | m/z (M + H)$^+$ |
|---|---|---|---|---|---|
| 36A | 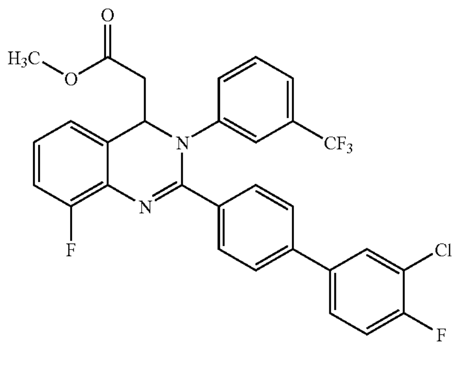 | 570.9 | 5.03 | 1 | 571 |
| 37A | 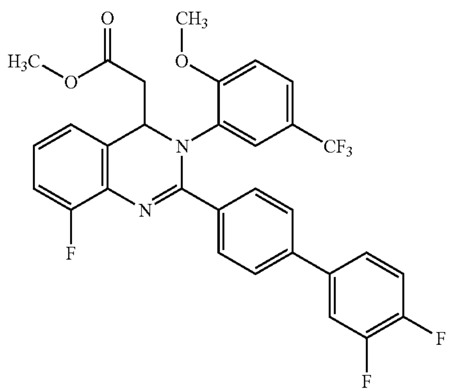 | 584.5 | 4.80 | 1 | 585 |
| 38A | 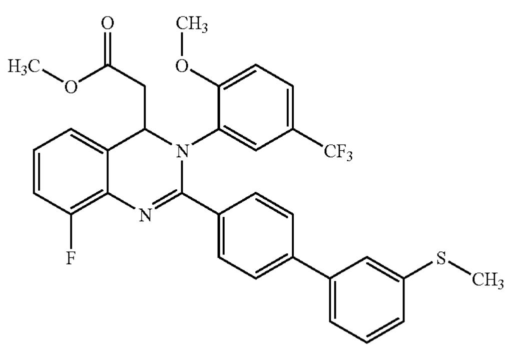 | 594.6 | 3.99 | 7 | 595 |
| 39A | 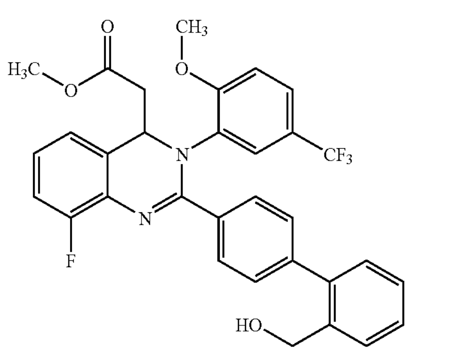 | 578.5 | 4.55 | 5 | 579 |

TABLE 1-continued

| Example | Structure | Molecular weight | HPLC R$_t$ [min] | HPLC/LCMS-method | m/z (M + H)$^+$ |
|---|---|---|---|---|---|
| 40A | 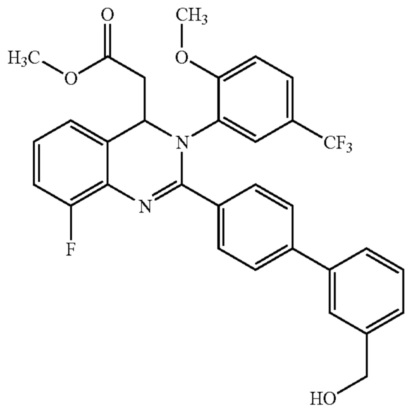 | 578.5 | 3.93 | 8 | 579 |
| 41A | 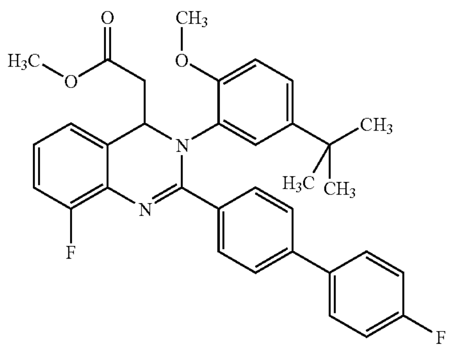 | 554.6 | 5.09 | 5 | 555 |
| 42A | 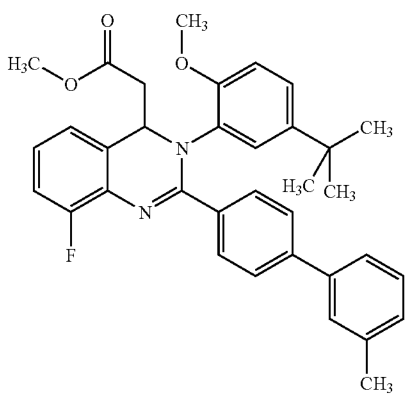 | 550.6 | 5.22 | 5 | 551 |
| 43A | 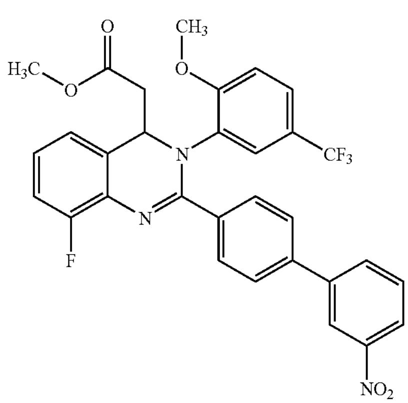 | 593.5 | 2.97 | 7 | 594 |

TABLE 1-continued

| Example | Structure | Molecular weight | HPLC $R_t$ [min] | HPLC/LCMS-method | m/z (M + H)+ |
|---|---|---|---|---|---|
| 44A | 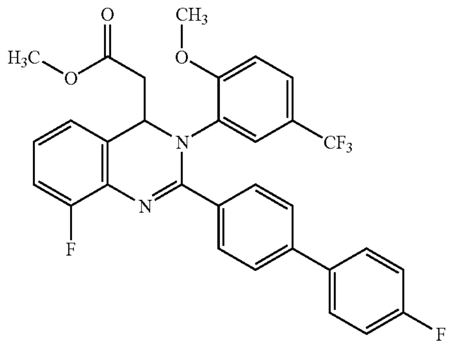 | 620.5 | 5.02 | 5 | 621 |

EXEMPLARY EMBODIMENTS

General Method [E]: Ester Hydrolysis of the Quinazolylacetic Esters 1.0 equivalent of the quinazolylacetic ester are dissolved in dioxane, and 5.0 equivalents of 1N sodium hydroxide solution are added. The mixture is stirred at 50° C. for 2 hours and, after the reaction is complete (reaction checked by analytical HPLC), is concentrated. The residue is then taken up in water and adjusted to pH=5 with 1N hydrochloric acid. The resulting precipitate is filtered off, washed with a little water and diethyl ether and dried under high vacuum at room temperature. Alternatively, the precipitate can be filtered through an Extrelut cartridge, washing with ethyl acetate, and the filtrate be concentrated. If the purity of the product is not high enough, it is purified by preparative HPLC on an RP phase (method 4).

Example 1

{8-Fluoro-2-(4'-fluoro-1,1'-biphenyl-4-yl)-3-[3-trifluoromethyl)phenyl]-3,4-dihydro-4-quinazolinyl}acetic acid

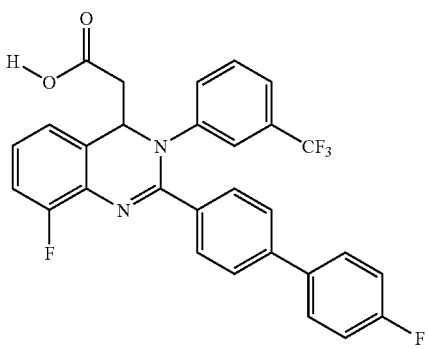

Starting from 1.13 g (2.1 mmol) of methyl ester from Example 14A, general method [E] results in 1.10 g (97% of theory) of product.

HPLC (method 1): $R_t$=4.64 min

MS (ESI-pos): m/z=523.4 (M+H)+

1H-NMR (200 MHz, CD3CN): δ [ppm]=7.83 (d, 2H); 7.68-7.57 (m, 5H); 7.33 (d, 2H); 7.28-7.19 (m, 5H); 7.05-7.01 (m, 1H); 5.55-5.47 (m, 1H); 2.87 (dd, 1H); 2.66 (dd, 1H).

Example 2

{8-Fluoro-2-(4'-fluoro-1,1'-biphenyl-4-yl)-3-[3-(trifluoromethyl)phenyl]-3,4-dihydro-4-quinazolinyl}acetic acid

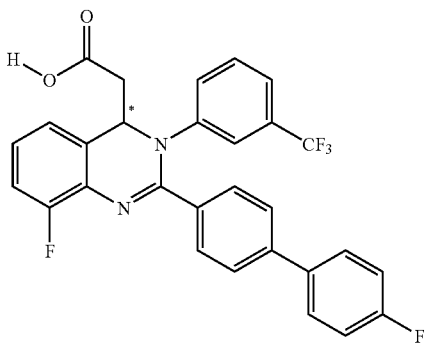

Separation of 359 mg of the racemate from Example 1 by method 2 results in 118 mg (66% of theory) of product.

HPLC (method 1): $R_t$=4.62 min

MS (ESI-pos): m/z=522.9 (M+H)+

1H-NMR (400 MHz, CD3CN): δ [ppm]=7.84 (d, 2H); 7.82 (d, 2H); 7.65-7.57 (m, 5H); 7.33-7.31 (m, 2H); 7.23-7.13 (m, 5H); 7.02 (d, 1H); 5.50 (t, 1H); 2.86 (dd, 1H); 2.67 (dd, 1H).

Example 3

{8-Fluoro-2-(3'-methyl-1,1'-biphenyl-4-yl)-3-[3-(trifluoromethyl)phenyl]-3,4-dihydro-4-quinazolinyl}acetic acid

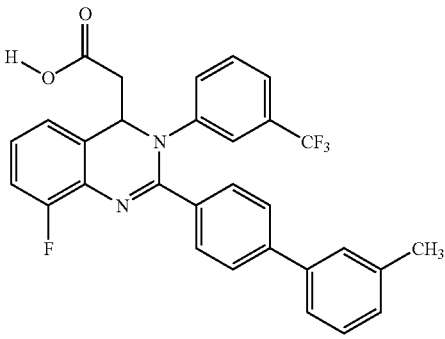

Starting from 1.13 g (2.1 mmol) of methyl ester from Example 15A, general method [E] results in 1.10 g (97% of theory) of product.

HPLC (method 1): $R_t$=4.74 min
MS (ESI-pos): m/z 519 (M+H)$^+$
$^1$H-NMR (400 MHz, CD$_3$CN): δ [ppm]=7.83 (s, 2H); 7.59 (s, 1H); 7.49 (d, 2H); 7.35-7.24 (m, 6H); 7.18-7.09 (m, 3H); 7.00 (d, 1H); 5.51 (t, 1H); 2.81-2.75 (m, 1H); 2.60-2.55 (m, 1H); signal for CH$_3$ group underneath solvent signal.

Example 4

{8-Fluoro-2-(3'-methyl-1,1'-biphenyl-4-yl)-3-[3-(trifluoromethyl)phenyl]-3,4-dihydro-4-quinazolinyl}acetic acid

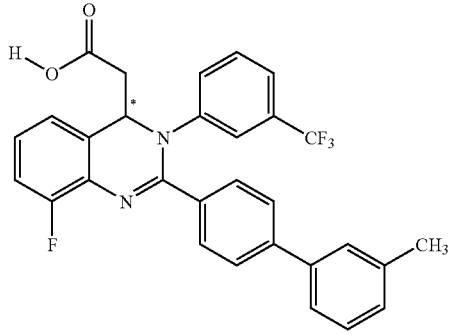

Separation of 2.48 g of the racemate from Example 3 by method 2 and renewed purification by preparative HPLC (method 4) result in 449 mg (36% of theory) of product.

HPLC (method 1): $R_t$=4.72 min
MS (ESI-pos): m/z=518.8 (M+H)$^+$
$^1$H-NMR (400 MHz, CD$_3$CN): δ [ppm]=7.83 (d, 2H); 7.61-7.59 (m, 3H); 7.45 (s, 1H); 7.41 (d, 1H); 7.35-7.31 (m, 3H); 7.24-7.14 (m, 4H); 7.02 (d, 1H); 5.50 (dd, 1H); 2.86 (dd, 1H); 2.67 (dd, 1H); 2.38 (s, 3H).

Example 5

{8-Fluoro-2-(4'-fluoro-3'-methyl-1,1'-biphenyl-4-yl)-3-[3-(trifluoromethyl)phenyl]-3,4-dihydro-4-quinazolinyl}acetic acid

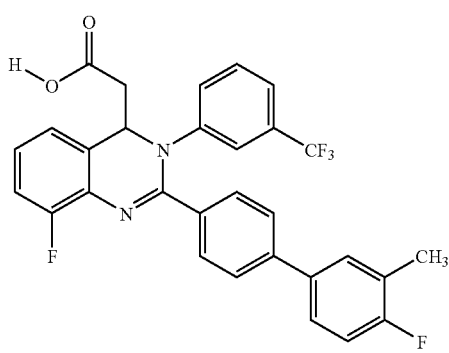

Starting from 80 mg (0.15 mmol) of methyl ester from Example 16A, general method [E] results in 36 mg (46% of theory) of product.

HPLC (method 1): $R_t$=4.75 min
MS (ESI-pos): m/z=537 (M+H)$^+$
$^1$H-NMR (300 MHz, CD$_3$CN): δ [ppm]=7.84-7.79 (m, 2H); 7.59-7.41 (m, 5H); 7.33-7.31 (m, 2H); 7.25-7.01 (m, 5H); 5.52-5.47 (m, 1H); 2.86 (dd, 1H); 2.68 (dd, 1H); 2.30 (s, 3H).

Example 6

{8-Fluoro-2-(3'-fluoro-1,1'-biphenyl-4-yl)-3-[3-(trifluoromethyl)phenyl]-3,4-dihydro-4-quinazolinyl}acetic acid

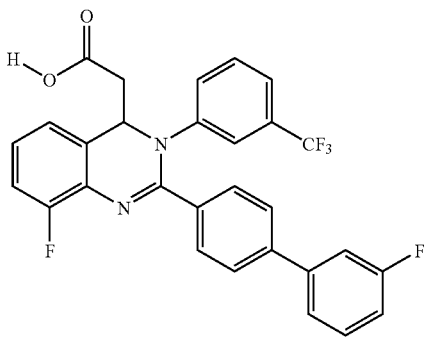

Starting from 80 mg (0.15 mmol) of methyl ester from Example 17A, general method [E] results in 75 mg (95% of theory) of product.

HPLC (method 1): $R_t$=4.61 min
MS (ESI-pos): m/z=523 (M+H)$^+$
$^1$H-NMR (300 MHz, CD$_3$CN): δ [ppm]=7.87-7.83 (m, 2H); 7.64-7.59 (m, 3H); 7.48-7.29 (m, 5H); 7.25-7.09 (m, 4H); 7.04-7.01 (m, 1H); 5.52-5.47 (m, 1H); 2.86 (dd, 1H); 2.68 (dd, 1H).

Example 7

{2-(3',4'-Difluoro-1,1'-biphenyl-4-yl)-8-fluoro-3-[3-(trifluoromethyl)phenyl]-3,4-dihydro-4-quinazolinyl}acetic acid

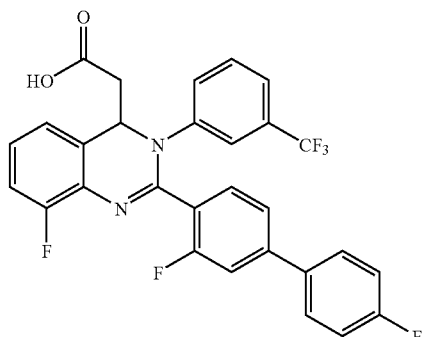

Starting from 15 mg (0.03 mmol) of methyl ester from Example 18A, general method [E] results in 14 mg (96% of theory) of product.

HPLC (method 1): $R_t$=4.65 min
MS (ESI-pos): m/z=541 (M+H)$^+$
$^1$H-NMR (400 MHz, CD$_3$CN): δ [ppm]=2.77 (dd, 1H); 3.02 (dd, 1H); 5.51 (t, 1H); 7.02 (d, 1H); 7.10-7.25 (m, 5H); 7.37 (s, 3H); 7.47-7.55 (m, 2H); 7.57-7.65 (m, 2H); 7.86 (dd, 1H).

Examples 8 to 29 in table 2 are prepared in analogy to general method [E].

TABLE 2

| Example | Structure | Molecular weight | HPLC R$_t$ [min] | HPLC/LCMS method | m/z (M + H)$^+$ |
|---|---|---|---|---|---|
| 8 | 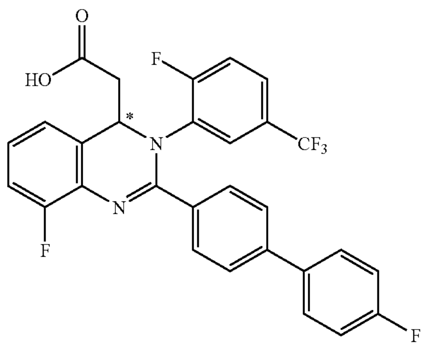 | 540.5 | 4.0 | 3 | 541 |
| 9 | 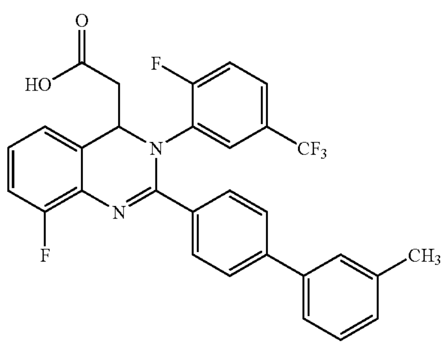 | 536.5 | 4.1 | 3 | 537 |
| 10 | 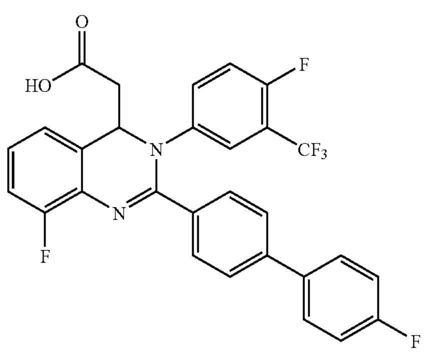 | 540.5 | 4.0 | 3 | 541 |
| 11 | 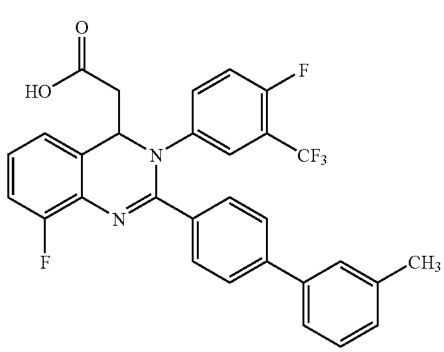 | 536.5 | 4.1 | 3 | 537 |

TABLE 2-continued

| Example | Structure | Molecular weight | HPLC R$_t$ [min] | HPLC/LCMS method | m/z (M + H)$^+$ |
|---|---|---|---|---|---|
| 12 | 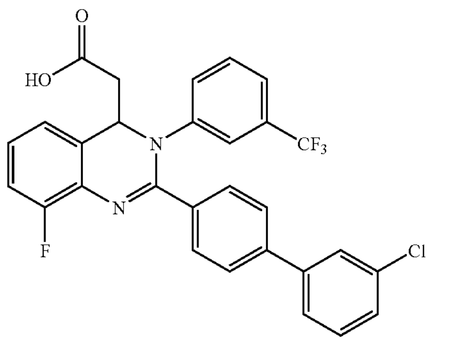 | 538.9 | 4.81 | 1 | 539 |
| 13 | 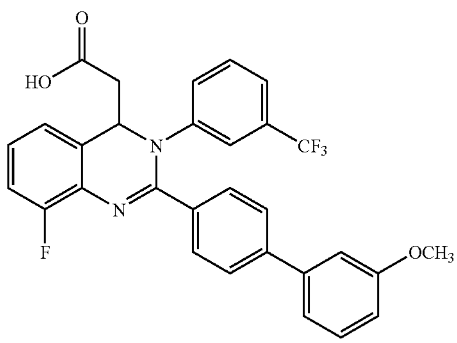 | 534.5 | 4.66 | 1 | 535 |
| 14 | 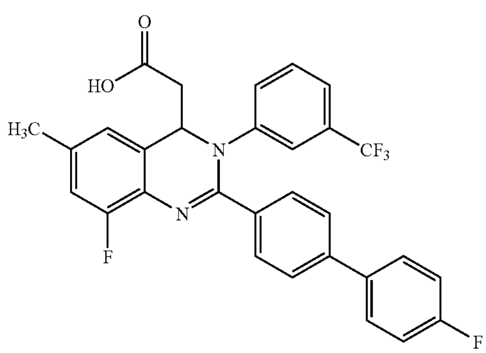 | 536.5 | 4.61 | 1 | 537 |
| 15 | 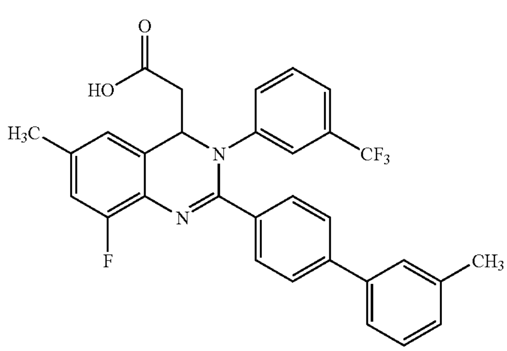 | 532.5 | 4.71 | 1 | 533 |

TABLE 2-continued

| Example | Structure | Molecular weight | HPLC R$_t$ [min] | HPLC/LCMS method | m/z (M + H)$^+$ |
|---|---|---|---|---|---|
| 16 | 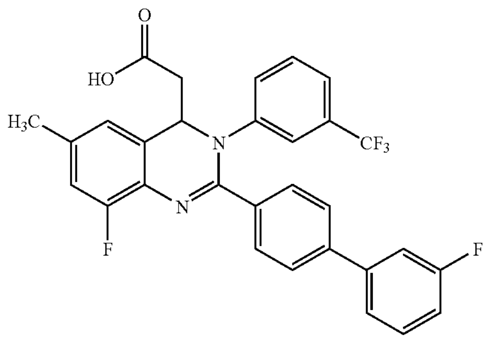 | 536.5 | 4.61 | 1 | 537 |
| 17 | 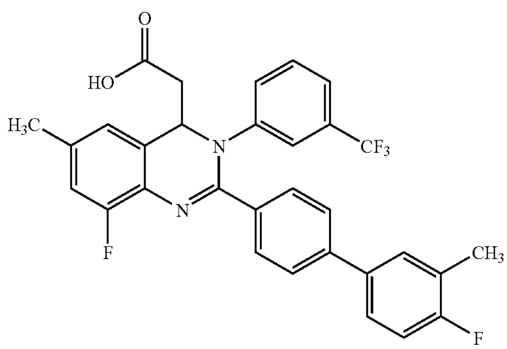 | 550.5 | 4.73 | 1 | 551 |
| 18 | 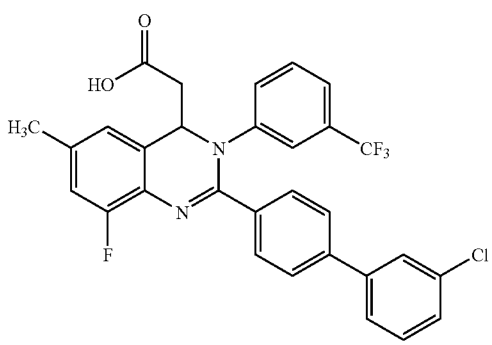 | 553.0 | 4.72 | 1 | 553 |
| 19 | 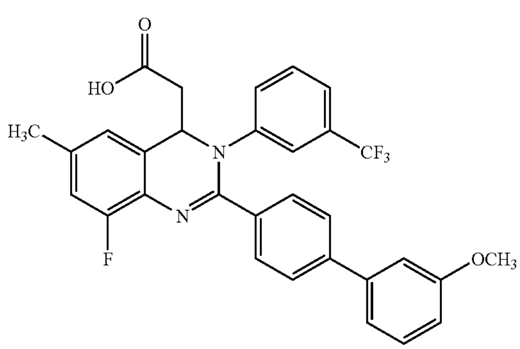 | 548.5 | 4.6 | 1 | 549 |

TABLE 2-continued

| Example | Structure | Molecular weight | HPLC R$_t$ [min] | HPLC/LCMS method | m/z (M + H)$^+$ |
|---|---|---|---|---|---|
| 20 | 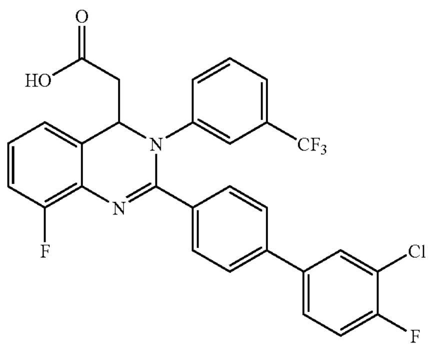 | 556.9 | 4.75 | 1 | 557 |
| 21 | 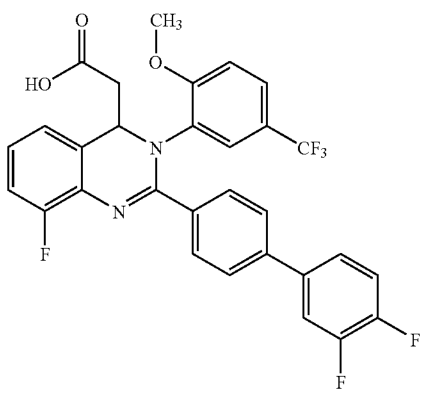 | 570.5 | 4.6 | 1 | 571 |
| 22 | 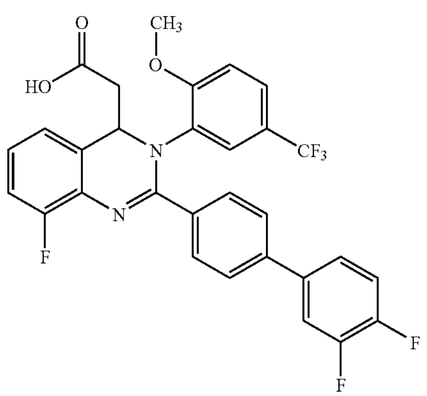 | 570.5 | 4.6 | 5 | 571 |
| 23 | 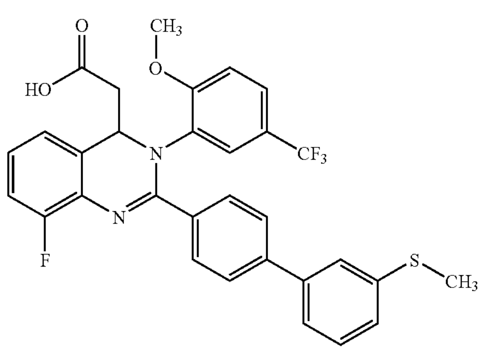 | 580.6 | 3.1 | 7 | 581 |

TABLE 2-continued
| Example | Structure | Molecular weight | HPLC R$_t$ [min] | HPLC/LCMS method | m/z (M + H)$^+$ |
|---|---|---|---|---|---|
| 24 | 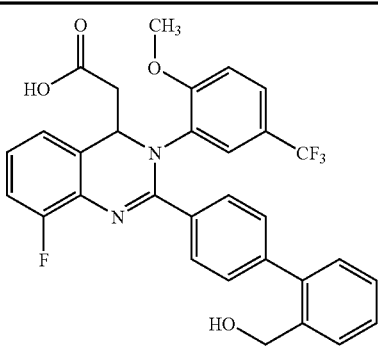 | 564.5 | 3.8 | 8 | 565 |
| 25 | 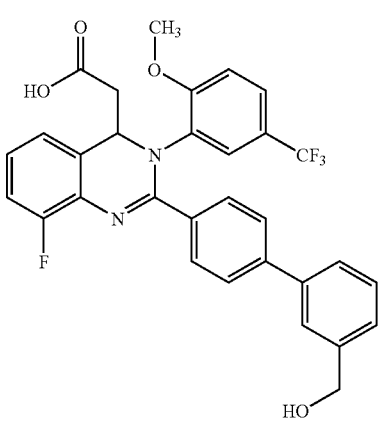 | 564.5 | 2.4 | 3 | 565 |
| 26 | 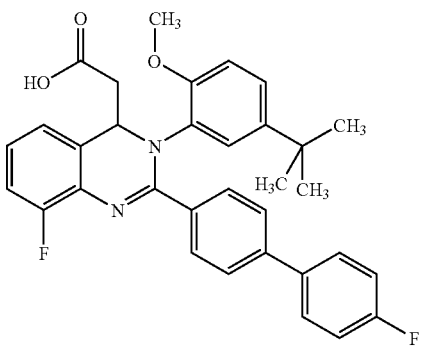 | 540.6 | 2.8 | 7 | 541 |
| 27 | 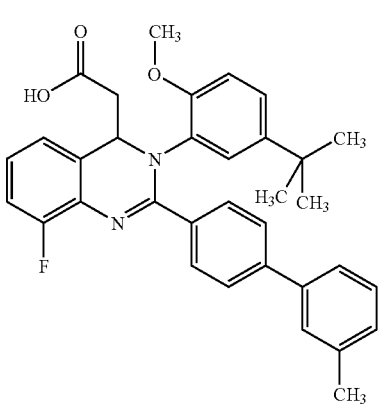 | 536.6 | 5.0 | 1 | 537 |

TABLE 2-continued

| Example | Structure | Molecular weight | HPLC R$_t$ [min] | HPLC/LCMS method | m/z (M + H)$^+$ |
|---------|-----------|------------------|------------------|------------------|-----------------|
| 28 | 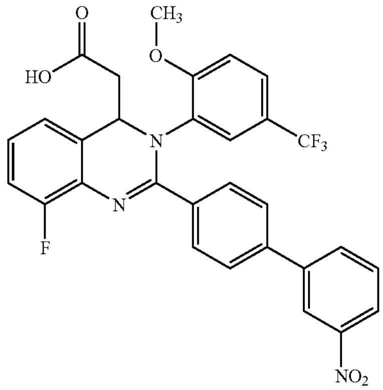 | 579.5 | 3.2 | 7 | 580 |
| 29 | 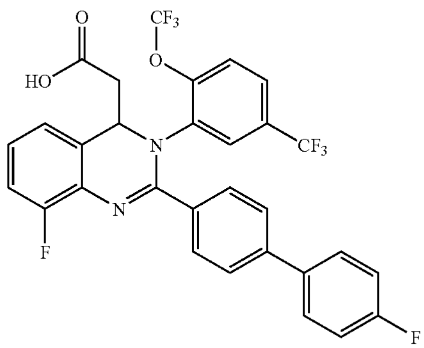 | 606.5 | 4.9 | 1 | 607 |

Example 30

{2-[4-(1,3-Benzodioxol-5-yl)phenyl]-8-fluoro-3-[2-methoxy-5-(trifluoromethyl)phenyl]-3,4-dihydro-4-quinazolinyl}acetic acid

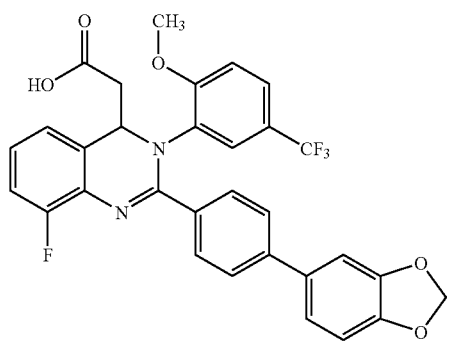

Starting from 56 mg (0.09 mmol) of methyl ester from Example 19A, general method [E] results in 52 mg (92% of theory) of product.

HPLC (method 7): R$_t$=3.13 min

MS (ESI-pos): m/z=579 (M+H)$^+$ $^1$H-NMR (400 MHz, CD$_3$CN): δ [ppm]=7.70 (d, 1H); 7.57 (d, 1H); 7.50-7.40 (m, 4H); 7.14-7.08 (m, 4H); 6.94-6.88 (m, 2H); 5.13 (dd, 1H); 3.60 (s, 3H); 3.05-3.00 (m, 2H); 2.62 (dd, 2H).

Example 31

{2-[4-(4-Fluorophenyl)phenyl]-8-fluoro-3-[2-methoxy-5-(trifluoromethyl)phenyl]-3,4-dihydro-4-quinazolinyl}acetic acid

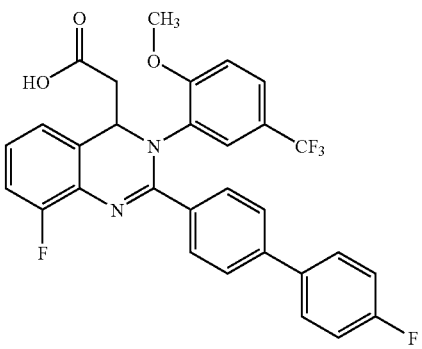

Starting from 38.90 (0.07 mmol) of the ester from Example 20A, reaction in analogy to general method [E] with 8.24 mg (0.21 mmol) of sodium hydroxide in 10 ml of dioxane results in 29 mg (76% of theory) of the target compound.

HPLC (method 1): R$_t$=4.6 min

MS (ESI-pos): m/z=353 (M+H)$^+$ $^1$H-NMR (200 MHz, DMSO-d$_6$): δ [ppm]=2.55-2.63 (m, 2H); 3.62 (s, 3H); 5.13-5.30 (m, 1H); 6.90-7.80 (m, 14H); 12.5-12.8 (br.s, 1H).

Example 32

{2-[4-(4-Fluorophenyl)phenyl]-8-fluoro-3-[2-methoxy-5-(trifluoromethyl)phenyl]-3,4-dihydro-4-quinazolinyl}acetic acid

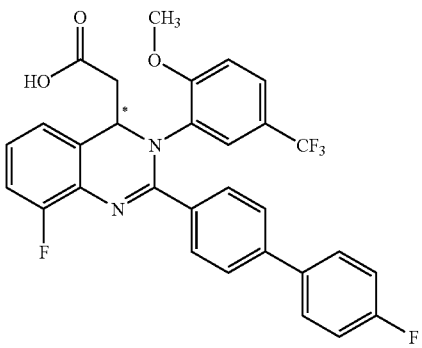

Separation of 172 mg of the racemate from Example 31 by method 9 and renewed purification by chromatography on silica gel (dichloromethane, dichloromethane/methanol 10:1) result in 60 mg (35% of theory) of the product.

HPLC (method 5): $R_t$=4.6 min

MS (ESI-pos): m/z=553 (M+H)$^+$ $^1$H-NMR (200 MHz, DMSO-d$_6$): δ [ppm]=2.60-2.90 (br.m, 2H); 3.10-3.80 (br.s, 3H); 5.00-5.20 (m, 1H); 6.80-7.80 (m, 14H).

Example 33

{2-[4-(3-Methylphenyl)phenyl]-8-fluoro-3-[2-methoxy-5-(trifluoromethyl)phenyl]-3,4-dihydro-4-quinazolinyl}acetic acid

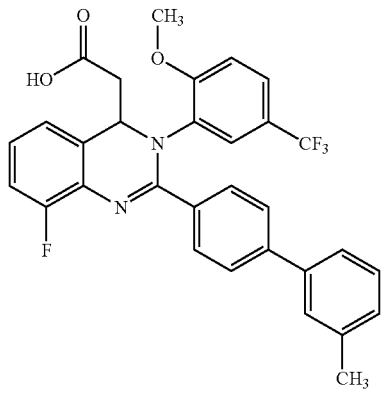

Starting from 450 mg (0.80 mmol) of the ester from Example 21A, reaction in analogy to general method [E] with 96 mg (2.40 mmol) of sodium hydroxide in 21.5 ml of dioxane results in 407.5 mg (93% of theory) of the target compound.

HPLC (method 1): $R_t$=4.7 min

MS (ESI-pos): m/z=549 (M+H)$^+$

Example 34

{2-[4-(3-Methylphenyl)phenyl]-8-fluoro-3-[2-methoxy-5-(trifluoromethyl)phenyl]-3,4-dihydro-4-quinazolinyl}acetic acid

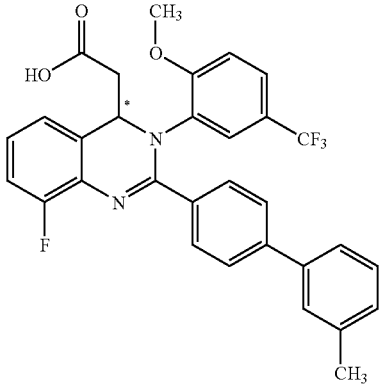

Separation of 407.5 mg of the racemate from Example 33 by method 10 and renewed purification by crystallization from diethyl ether result in 153.6 mg (38% of theory) of the product.

HPLC (method 5): $R_t$=4.7 min

MS (ESI-pos): m/z=549 (M+H)$^+$ $^1$H-NMR (300 MHz, DMSO-d$_6$): δ [ppm]=2.35 (s, 3H); 2.50-2.60 (m, 1H); 2.90-3.10 (m, 1H); 3.40-3.80 (br.s, 3H); 5.10-5.20 (m, 1H); 6.90-7.75 (m, 14H); 12.5-12.7 (br.s, 1H).

Example 35

{2-[4-(3-Methoxyphenyl)phenyl]-8-fluoro-3-[2-methoxy-5-(trifluoromethyl)phenyl]-3,4-dihydro-4-quinazolinyl}acetic acid

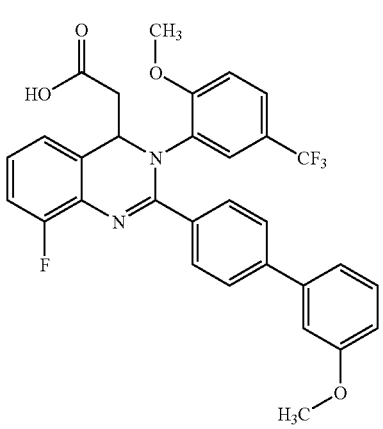

Starting from 459 mg (0.79 mmol) of the ester from Example 22A, reaction in analogy to general method [E] with 95.2 mg (2.38 mmol) of sodium hydroxide in 54 ml of dioxane results in 383 mg (86% of theory) of the target compound.

HPLC (method 1): $R_t$=4.5 min

MS (ESI-pos): m/z=565 (M+H)$^+$

Example 36

{2-[4-(3-Methoxyphenyl)phenyl]-8-fluoro-3-[2-methoxy-5-(trifluoromethyl)phenyl]-3,4-dihydro-4-quinazolinyl}acetic acid

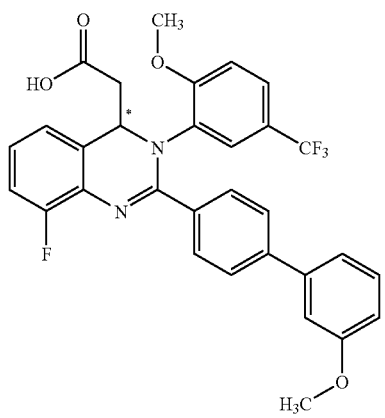

Separation of 46 mg of the racemate from Example 35 by method 6 and renewed purification by crystallization from diethyl ether result in 13 mg (28% of theory) of the product.

HPLC (method 5): $R_t$=4.6 min

MS (ESI-pos): m/z=565 (M+H)$^+$ $^1$H-NMR (300 MHz, DMSO-d$_6$): δ [ppm]=2.50-2.60 (m, 1H); 2.90-3.10 (m, 1H); 3.30 (s, 3H); 3.80 (s, 3H); 5.10-5.20 (m, 1H); 6.90-7.75 (m, 14H); 12.5-12.7 (br.s, 1H).

Example 37

{2-[4-(3-Fluorophenyl)phenyl]-8-fluoro-3-[2-methoxy-5-(trifluoromethyl)phenyl]-3,4-dihydro-4-quinazolinyl}acetic acid

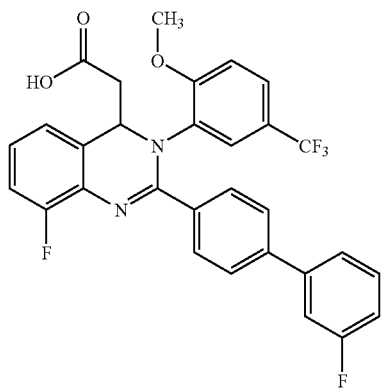

Starting from 20.00 (mg (0.04 mmol) of the ester from Example 23A, reaction in analogy to general method [E] with 4.24 mg (0.11 mmol) of sodium hydroxide in 10 ml of dioxane results in 18.7 mg (96% of theory) of the target compound.

HPLC (method 5): $R_t$=4.6 min

MS (ESI-pos): m/z=553 (M+H)$^+$ $^1$H-NMR (300 MHz, DMSO-d$_6$): δ [ppm]=2.50-2.65 (m, 1H); 2.90-3.10 (m, 1H); 3.50-3.7 (br.s, 3H); 3.80 (s, 3H); 5.10-5.20 (m, 1H); 6.90-7.75 (m, 14H); 12.50-12.60 (br.s, 1H).

B. ASSESSMENT OF THE PHYSIOLOGICAL ACTIVITY

The in vitro effect of the compounds of the invention can be shown in the following assays:

Anti-HCMV (Anti-Human Cytomegalovirus) Cytopathogenicity Tests

The test compounds are employed as 50 millimolar (mM) solutions in dimethyl sulfoxide (DMSO). Ganciclovir, foscamet and cidofovir are used as reference compounds. After addition of in each case 2 µl of the 50, 5, 0.5 and 0.05 mM DMSO stock solutions to 98 µl portions of cell culture medium in row 2 A-H for duplicate determinations, 1:2 dilutions are carried out with 50 µl portions of medium up to row 11 of the 96-well plate. The wells in rows 1 and 12 each contain 50 µl of medium. 150 µl of a suspension of 1×10$^4$ cells (human prepuce fibroblasts [NHDF]) are then pipetted into each of the wells (row 1=cell control) and, in rows 2-12, a mixture of HCMV-infected and uninfected NHDF cells (M.O.I.=0.001-0.002), i.e. 1-2 infected cells per 1000 uninfected cells. Row 12 (without substance) serves as virus control. The final test concentrations are 250-0.0005 µM. The plates are incubated at 37° C./5% CO$_2$ for 6 days, i.e. until all the cells are infected in the virus controls (100% cytopathogenic effect [CPE]). The wells are then fixed and stained by adding a mixture of formalin and Giemsa's dye (30 minutes), washed with double-distilled water and dried in a drying oven at 50° C. The plates are then assessed visually using an overhead microscope (plaque multiplier from Technomara).

The following data can be acquired from the test plates:

CC$_{50}$ (NHDF)=substance concentration in 1M at which no visible cytotoxic effects on the cells are evident by comparison with the untreated cell control;

EC$_{50}$ (HCMV)=substance concentration in µM which inhibits the CPE (cytopathic effect) by 50% compared with the untreated virus control;

SI (selectivity index)=CC$_{50}$ (NHDF)/EC$_{50}$ (HCMV).

Representative in vitro data for the effects of the compounds of the invention are shown in table A:

TABLE A

| Example No. | NHDF CC$_{50}$ [µM] | HCMV EC$_{50}$ [µM] | SI HCMV |
|---|---|---|---|
| 1 | 15 | 0.1 | 150 |
| 2 | 12 | 0.07 | 171 |
| 3 | 15 | 0.13 | 115 |
| 4 | 8.6 | 0.06 | 143 |
| 5 | 12 | 0.74 | 16 |
| 6 | 12 | 0.35 | 34 |
| 7 | 31 | 1.8 | 17 |
| 32 | 15 | 0.01 | 1500 |
| 36 | 15 | 0.01 | 1500 |

The suitability of the compounds of the invention for the treatment of HCMV infections can be shown in the following animal model:

HCMV Xenograft Gelfoam® Model

Animals:

3-4-week old female immunodeficient mice (16-18 g), Fox Chase SCID or Fox Chase SCID-NOD or SCID beige, are purchased from commercial breeders (Bomholtgaard, Jackson). The animals are housed under sterile conditions (including bedding and feed) in isolators.

Virus Growing:

Human cytomegalovirus (HCMV), Davis strain, is grown in vitro on human embryonic prepuce fibroblasts (NHDF cells). After the NHDF cells have been infected with a multiplicity of infection (M.O.I.) of 0.01, the virus-infected cells are harvested 5-7 days later and stored in the presence of minimal essential medium (MEM), 10% fetal calf serum (FCS) with 10% DMSO at 40° C. After serial ten-fold dilutions of the virus-infected cells, the titer is determined on 24-well plates of confluent NHDF cells after vital staining with neutral red, or fixing and staining with a formalin-Giemsa mixture (as described under B).

Preparation of the Sponges, Transplantation, Treatment and Evaluation:

Collagen sponges 1×1×1 cm in size (Gelfoam®; from Peasel & Lorey, order No. 407534; K. T. Chong et al., Abstracts of 39$^{th}$ Interscience Conference on Antimicrobial Agents and Chemotherapy, 1999, p. 439; P. M. Kraemer et al, Cancer Research 1983, (43): 4822-4827) are initially wetted with phosphate-buffered saline (PBS), the trapped air bubbles are removed by degassing, and then stored in MEM+10% FCS. 1×10$^6$ virus-infected NHDF cells (infection with HCMV Davis M.O.I.=0.01) are detached 3 hours after infection and added in a drop of 20 µl of MEM, 10% FCS, to a moist sponge. Optionally, after 12-13 hours 5 ng/µl basic fibroblast growth factor (bFGF) in 25 µl of PBS/0.1% BSA/1 mM DTT are put on infected sponges and incubated for 1 hour. For the transplantation, the immunodeficient mice are anesthetized with Avertin or a azepromazine-xylazine and ketamine mixture, the fur on the back is removed using a dry shaver, the epidermis is opened 1-2 cm, unstressed and the moist sponges are transplanted under the dorsal skin. The surgical wound is closed with tissue glue. 24 hours after the transplantation, the mice are treated orally with the substance three times a day (7.00 h and 14.00 h and 19.00 h) twice a day (8 h and 18 h) or once a day (14 h) over a period of 8 days. The daily dose is for example 3 or 10 or 30 or 100 mg/kg of body weight, the volume administered is 10 ml/kg of body weight. The substances are formulated in the form of a 0.5% strength Tylose suspension optionally with 2% DMSO. 9 days after transplantation and 16 hours after the last administration of substance, the animals are painlessly sacrificed and the sponge is removed. The virus-infected cells are released from the sponge by collagenase digestion (330 U/1.5 ml) and stored in the presence of MEM, 10% fetal calf serum, 10% DMSO at −140° C. Evaluation takes place after serial ten-fold dilutions of the virus-infected cells by determining the titer on 24-well plates of confluent NHDF cells after vital staining with neutral red, or fixing and staining with a formalin-Giemsa mixture (as described under B). The number of infectious virus particles after the substance treatment compared with the placebo-treated control group is determined.

C. EXEMPLARY EMBODIMENTS OF PHARMACEUTICAL COMPOSITIONS

The compounds of the invention can be converted into pharmaceutical preparations in the following ways:

Tablet:

Composition:

100 mg of the compound of Example 1, 50 mg of lactose (monohydrate), 50 mg of corn starch (native), 10 mg of polyvinylpyrolidone (PVP 25) (from BASF, Ludwigshafen, Germany) and 2 mg of magnesium stearate.

Tablet weight 212 mg. Diameter 8 mm, radius of curvature 12 mm.

Production:

The mixture of active ingredient, lactose and starch is granulated with a 5% strength solution (m/m) of the PVP in water. The granules are then dried and mixed with the magnesium stearate for 5 min. This mixture is compressed using a conventional tablet press (see above for format of the tablet). A guideline for the compressive force used for the compression is 15 kN.

Suspension which can be Administered Orally:

Composition:

1000 mg of the compound of Example 1, 1000 mg of ethanol (96%), 400 mg of Rhodigel (xanthan gum from FMC, Pennsylvania, USA) and 99 g of water.

10 ml of oral suspension are equivalent to a single dose of 100 mg of the compound of the invention.

Production:

The Rhodigel is suspended in ethanol, and the active ingredient is added to the suspension. The water is added while stirring. The mixture is stirred for about 6 h until the swelling of the Rhodigel is complete.

The invention claimed is:

1. A compound of the formula

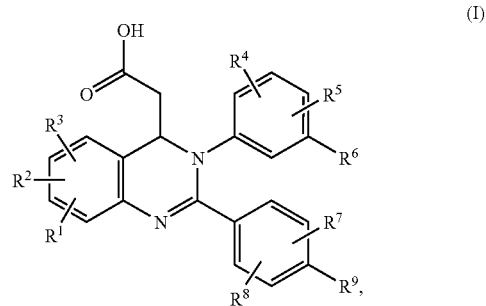

in which
R$^1$, R$^2$ and R$^3$ are independently of one another hydrogen, alkyl, alkoxy, carboxyl, alkylcarbonyl, alkoxycarbonyl, aminocarbonyl, trifluoromethyl, halogen, cyano, hydroxy or nitro,
R$^4$ and R$^5$ are independently of one another hydrogen, alkyl, alkoxy, cyano, halogen, nitro, trifluoromethyl or trifluoromethoxy,
R$^6$ is alkyl, cyano, halogen, nitro or trifluoromethyl,
R$^7$ and R$^8$ are independently of one another hydrogen, halogen, alkyl or alkoxy, and
R$^9$ is aryl or 1,3-benzodioxol-5-yl in which aryl and 1,3-benzodioxol-5-yl may be substituted by 1 to 3 substituents, where the substituents are selected independently of one another from the group consisting of alkyl, alkoxy, alkylthio, carboxyl, alkylcarbonyl, alkoxycarbonyl, aminocarbonyl, trifluoromethyl, halogen, carbamoyl, cyano, hydroxy, amino, alkylamino, nitro and optionally hydroxy-substituted alkyl,
or a salt thereof.

2. A compound according to claim 1, in which
R$^1$, R$^2$ and R$^3$ are independently of one another hydrogen, fluorine, chlorine, cyano, hydroxy, aminocarbonyl or nitro,
R$^4$ and R$^5$ are independently of one another hydrogen, fluorine, alkyl or alkoxy,
R$^6$ is trifluoromethyl, isopropyl or tert-butyl,
R$^7$ and R$^8$ are independently of one another hydrogen, halogen, C$_1$-C$_3$-alkyl or C$_1$-C$_3$-alkoxy, and
R$^9$ is phenyl or 1,3-benzodioxol-5-yl in which phenyl may be substituted by 1 to 3 substituents, where the substituents are selected independently of one another from the group consisting of C$_1$-C$_6$-alkyl, C$_1$-C$_6$-alkoxy, carboxyl, $C_1$-$C_6$-alkylcarbonyl, $C_1$-$C_6$-alkoxycarbonyl, trifluoromethyl, fluorine, chlorine, bromine, cyano, hydroxy, amino, $C_1$-$C_6$-alkylamino and nitro,
or a salt thereof.

3. A compound according to claim 1, in which
$R^1$ and $R^2$ are hydrogen,
$R^3$ is fluorine,
$R^4$ and $R^5$ are independently of one another hydrogen, fluorine or alkoxy,
$R^6$ is trifluoromethyl,
$R^7$ and $R^8$ are hydrogen and
$R^9$ is phenyl, in which phenyl may be substituted by 1 or 2 substituents, where the substituents are selected independently of one another from the group consisting of methyl, methoxy, fluorine and chlorine,
or a salt thereof.

4. A process for preparing a compound of the formula (I) as claimed in claim 1, comprising the step of reacting a compound of the formula

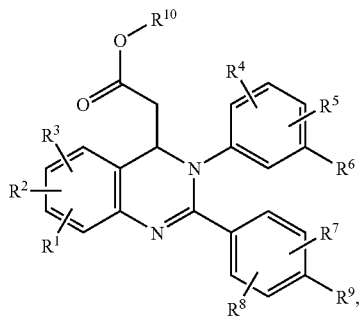

(II)

in which
$R^1$, $R^2$, $R^3$, $R^4$, $R^5$, $R^6$, $R^7$, $R^8$ and $R^9$ have the meaning indicated in claim 1, and
$R^{10}$ is alkyl, with a base.

5. A pharmaceutical composition comprising a compound according to claim 1 in combination with an inert, nontoxic, pharmaceutically suitable excipient.

6. A pharmaceutical composition according to claim 5 for the treatment of viral infections.

7. A method for treating viral infections in humans and animals by administering an antivirally effective amount of at least one compound according to claim 1.

8. The method of claim 7 wherein said infection is caused by a virus of the group Herpes viridae.

9. The method of claim 8 wherein said virus is a cytomegalovirus.

10. The method of claim 9 wherein said virus is human cytomegalovirus (HCMV).

11. A method for controlling viral infections in humans and animals by administering an antivirally effective amount of a pharmaceutical composition according to claim 5.

12. The method of claim 11 wherein said infection is caused by a virus of the group Herpes viridae.

13. The method of claim 12 wherein said virus is a cytomegalovirus.

14. The method of claim 13 wherein said virus is human cytomegalovirus (HCMV).

15. The process of claim 4 wherein $R^{10}$ is methyl or ethyl.

* * * * *